United States Patent
Khan et al.

(10) Patent No.: US 12,178,524 B2
(45) Date of Patent: Dec. 31, 2024

(54) SYSTEM AND METHOD TO CONDUCT BONE SURGERY

(71) Applicants: NAVISECT, INC., Manorville, NY (US); The Research Foundation for the State University., Albany, NY (US)

(72) Inventors: Fazel Khan, East Setauket, NY (US); Michael Bielski, Manorville, NY (US); Jafar Khan, Stony Brook, NY (US); Imin Kao, Stony Brook, NY (US); Guangyu He, Port Jefferson Station, NY (US)

(73) Assignees: Navisect, Inc., Manorville, NY (US); The Research Foundation for The State University of New York_, Albany, NY (US)

( * ) Notice: Subject to any disclaimer, the term of this patent is extended or adjusted under 35 U.S.C. 154(b) by 0 days.

(21) Appl. No.: 18/180,257

(22) Filed: Mar. 8, 2023

(65) Prior Publication Data

US 2023/0210609 A1    Jul. 6, 2023

Related U.S. Application Data

(63) Continuation of application No. 16/854,804, filed on Apr. 21, 2020, now Pat. No. 11,602,397.
(Continued)

(51) Int. Cl.
*A61B 34/20* (2016.01)
*A61B 90/00* (2016.01)
(Continued)

(52) U.S. Cl.
CPC ............. *A61B 34/20* (2016.02); *A61B 90/30* (2016.02); *A61B 90/39* (2016.02); *A61B 90/96* (2016.02);
(Continued)

(58) Field of Classification Search
CPC ..... A61B 17/15; A61B 17/154; A61B 17/155; A61B 34/20; A61B 2034/2046;
(Continued)

(56) References Cited

U.S. PATENT DOCUMENTS 10,842,588 B2 * 11/2020 Hansen ................. A61B 90/30
11,351,007 B1    6/2022 Meftah et al.
(Continued)

FOREIGN PATENT DOCUMENTS

CN    110430809 A    11/2019
CN    111329552 A    6/2020
(Continued)

OTHER PUBLICATIONS

International Search Report of International Application No. PCT/US20/29164 mailed Jul. 13, 2020.
(Continued)

*Primary Examiner* — Eric S Gibson
(74) *Attorney, Agent, or Firm* — Hoffmann & Baron, LLP

(57) ABSTRACT

A surgical system is provided. The surgical system includes a camera operable to capture images and/or video. A projector is operable to project light, and a controller is communicatively coupled with the camera and the projector. The controller is operable to track movement of bone in real-time during surgery based on the images and/or video captured by the camera, and control the projector to project the light including a cutting line on the bone to indicate a cutting plane for cutting the bone during surgery.

11 Claims, 29 Drawing Sheets

Related U.S. Application Data

(60) Provisional application No. 63/012,617, filed on Apr. 20, 2020, provisional application No. 62/836,824, filed on Apr. 22, 2019.

(51) Int. Cl.
  *A61B 90/30* (2016.01)
  *A61B 90/96* (2016.01)
  *A61B 17/90* (2006.01)
  *A61B 34/10* (2016.01)

(52) U.S. Cl.
  CPC ......... *A61B 17/90* (2021.08); *A61B 2034/107* (2016.02); *A61B 2034/2055* (2016.02); *A61B 2034/2065* (2016.02)

(58) Field of Classification Search
  CPC .... A61B 2034/2048; A61B 2034/2055; A61B 2034/2057; A61B 90/30; A61B 90/96
  See application file for complete search history.

(56) References Cited

U.S. PATENT DOCUMENTS

| | | | |
|---|---|---|---|
| 11,432,828 B1 | 9/2022 | Lang | |
| 11,553,969 B1 | 1/2023 | Lang et al. | |
| 11,602,397 B2* | 3/2023 | Khan | A61B 34/20 |
| 2007/0073136 A1 | 3/2007 | Metzger | |
| 2014/0010747 A1 | 4/2014 | Haider et al. | |
| 2014/0107471 A1* | 4/2014 | Haider | A61B 5/1076 606/82 |
| 2016/0022374 A1 | 1/2016 | Hader et al. | |
| 2016/0100908 A1 | 4/2016 | Tesar | |
| 2017/0055819 A1* | 3/2017 | Hansen | A61B 17/062 |
| 2017/0086940 A1* | 3/2017 | Nakamura | A61B 90/36 |
| 2017/0196641 A1* | 7/2017 | Jagga | A61B 90/10 |
| 2017/0296178 A1 | 10/2017 | Miller et al. | |
| 2017/0312035 A1* | 11/2017 | May | A61B 90/90 |
| 2018/0011672 A1 | 5/2018 | Lang | |
| 2018/0116728 A1* | 5/2018 | Lang | A61B 17/155 |
| 2018/0168740 A1* | 6/2018 | Ryan | A61B 90/36 |
| 2018/0325618 A1 | 11/2018 | Justin et al. | |
| 2019/0008603 A1* | 1/2019 | Hansen | A61B 17/062 |
| 2019/0290297 A1* | 9/2019 | Haider | A61B 34/20 |
| 2020/0360093 A1* | 11/2020 | Khan | A61B 90/39 |
| 2021/0093413 A1 | 4/2021 | Poltaretskyi et al. | |
| 2021/0192763 A1* | 6/2021 | Liu | H04N 13/239 |
| 2021/0196383 A1* | 7/2021 | Shelton, IV | G16H 20/40 |
| 2021/0307765 A1 | 10/2021 | Dumpe et al. | |
| 2022/0008139 A1 | 1/2022 | Marti et al. | |
| 2022/0087749 A1 | 3/2022 | Marti et al. | |
| 2022/0117669 A1 | 4/2022 | Nikou et al. | |
| 2022/0125535 A1 | 4/2022 | Janna et al. | |
| 2022/0159227 A1 | 5/2022 | Casa | |
| 2022/0160440 A1 | 5/2022 | Jaramaz et al. | |
| 2022/0183762 A1 | 6/2022 | Nikou | |
| 2022/0265362 A1* | 8/2022 | Marti | G06T 7/70 |
| 2022/0296302 A1* | 9/2022 | Bleunven | A61B 90/14 |
| 2022/0338935 A1 | 10/2022 | Bell | |
| 2022/0346970 A1 | 11/2022 | Nikou | |
| 2022/0361960 A1 | 11/2022 | Poltaretskyi et al. | |
| 2022/0409298 A1 | 12/2022 | Haider et al. | |
| 2023/0016940 A1 | 1/2023 | Lang | |
| 2023/0210609 A1* | 7/2023 | Khan | A61B 34/20 606/87 |

FOREIGN PATENT DOCUMENTS

| | | | | |
|---|---|---|---|---|
| CN | 114098969 B | 5/2022 | | |
| CN | 115136253 A | 9/2022 | | |
| CN | 115426971 A | 12/2022 | | |
| EP | 3827777 A2 | 6/2021 | | |
| EP | 4003205 A1 | 6/2022 | | |
| EP | 3958782 A1 | 1/2023 | | |
| JP | 2018509993 A | 4/2014 | | |
| JP | 2014533964 A | 12/2014 | | |
| JP | 2021526940 A | 10/2021 | | |
| WO | 2014144780 A1 | 9/2014 | | |
| WO | 2014151474 A1 | 9/2014 | | |
| WO | 2016/205915 A1 | 12/2016 | | |
| WO | WO-2017114538 A1 * | 7/2017 | ............... | A61B 1/06 |
| WO | 2020102665 A1 | 5/2020 | | |
| WO | 2020219473 A1 | 10/2020 | | |
| WO | 2021076560 A1 | 4/2021 | | |
| WO | 2021127161 A1 | 6/2021 | | |
| WO | 2021203077 A1 | 10/2021 | | |
| WO | 2021257672 A1 | 12/2021 | | |
| WO | 2022076790 A1 | 4/2022 | | |

OTHER PUBLICATIONS

Report on a novel bone registration method: A rapid, accurate, and radiation-free technique for computer- and robotic-assisted orthopedic surgeries; Guangyu He et al.; Journal of Orthopaedics 23 (2021) 227-232.

Mannan A, Vun J, Lodge C, Eyre-Brook A, Jones S. Increased precision of coronal plane outcomes in robotic-assisted total knee arthroplasty: a systematic review and meta-analysis. Surgeon. Aug. 1, 2018; 16(4):237-244.

Khan F, Pearle A, Lightcap C, Boland PJ, Healey JH. Haptic robot-assisted surgery improves accuracy of wide resection of bone tumors: a pilot study. Clin Orthop Relat Res. Mar. 1, 2013;471(3):851-859.

Lavallee S. Registration for computer-integrated surgery: methodology. Comput Integrated Surg: Technol Clin Applicat. 1996;77.

Zheng G, Kowal J, Ballester MA, Caversaccio M, Nolte LP. (i) Registration techniques for computer navigation. Curr Orthop. Jun. 1, 2007;21(3):170-179.

Zheng G, Nolte LP. Computer-assisted orthopedic surgery: current state and future perspective. Front Surg. Dec. 23, 2015;2:66.

Eggers G, Kress B, Mühling J. Fully automated registration of intraoperative computed tomography image data for image-guided craniofacial surgery. J Oral Maxillofac Surg. Aug. 1, 2008;66(8): 1754-1760.

Geng J. Structured-light 3D surface imaging: a tutorial. Adv Optic Photon. Jun. 30, 2011;3(2):128-160.

Chan B, Auyeung J, Rudan JF, Ellis RE, Kunz M. Intraoperative application of hand-held structured light scanning: a feasibility study. Int J Comput Assisted Radiol Surg. Jun. 1, 2016;11(6): 1101-1108.

Paunipagar BK, Rasalkar DD. Imaging of articular cartilage. Indian J Radiol Imag. Jul. 2014; 24(3):237.

Boas FE, Fleischmann D. CT artifacts: causes and reduction techniques. Imag Med. Apr. 2, 2012;4(2):229-240.

European Search Report of European Application No. EP 20794513.0, mailed Dec. 13, 2022.

Drost B, Ulrich M, Navab N, Ilic S. Model globally, match locally: efficient and robust 3D object recognition. In: In2010 IEEE Computer Society Conference on Computer Vision and Pattern Recognition. Ieee; Jun. 13, 2010:998-1005.

Stoll KE, Miles JD, White JK, Punt SE, Conrad EU, Ching RP. Assessment of registration accuracy during computer-aided oncologic limb-salvage surgery. Int J Comput Assisted Radiol Surg. Sep. 1, 2015;10(9):1469-1475.

Zhang Z. Iterative point matching for registration of free-form curves and surfaces. Int J Comput Vis. Oct. 1, 1994;13(2):119-152.

* cited by examiner

SYSTEM AND METHOD TO CONDUCT BONE SURGERY

CROSS-REFERENCE TO RELATED APPLICATION

This application is a continuation of U.S. application Ser. No. 16/854,804, filed Apr. 21, 2020, which claims the benefit of U.S. Provisional Patent Application No. 62/836,824, filed in the U.S. Patent and Trademark Office on Apr. 22, 2019, and U.S. Provisional Patent Application No. 63/012,617, filed in the U.S. Patent and Trademark Office on Apr. 20, 2020, each of which is incorporated herein by reference in its entirety for all purposes.

FIELD

The present disclosure relates generally to systems and methods to conduct bone surgery. In at least one example, the present disclosure relates to systems and methods to conduct bone surgery with projected guidance.

BACKGROUND

In orthopedic surgery, surgeons can, before the actual surgery, obtain images of the patient's bone. For example, the images may be captured by X-ray, CT scan, and/or MRI scan. With the images, a 3D digital reconstruction of the bone can be obtained. The surgeon can then digitally determine a preoperative plan such as drawing on a computer annotation lines and/or resection plane(s) to outline precisely a surgical resection plan.

The surgeon then attempts to reproduce the preoperative plan at the time of surgery. For example, a surgeon may use tools such as rulers and/or mechanically based jigs and estimate locations based on palpable or visible landmarks.

BRIEF DESCRIPTION OF THE DRAWINGS

Implementations of the present technology will now be described, by way of example only, with reference to the attached figures, wherein.

DETAILED DESCRIPTION

Figure 1:
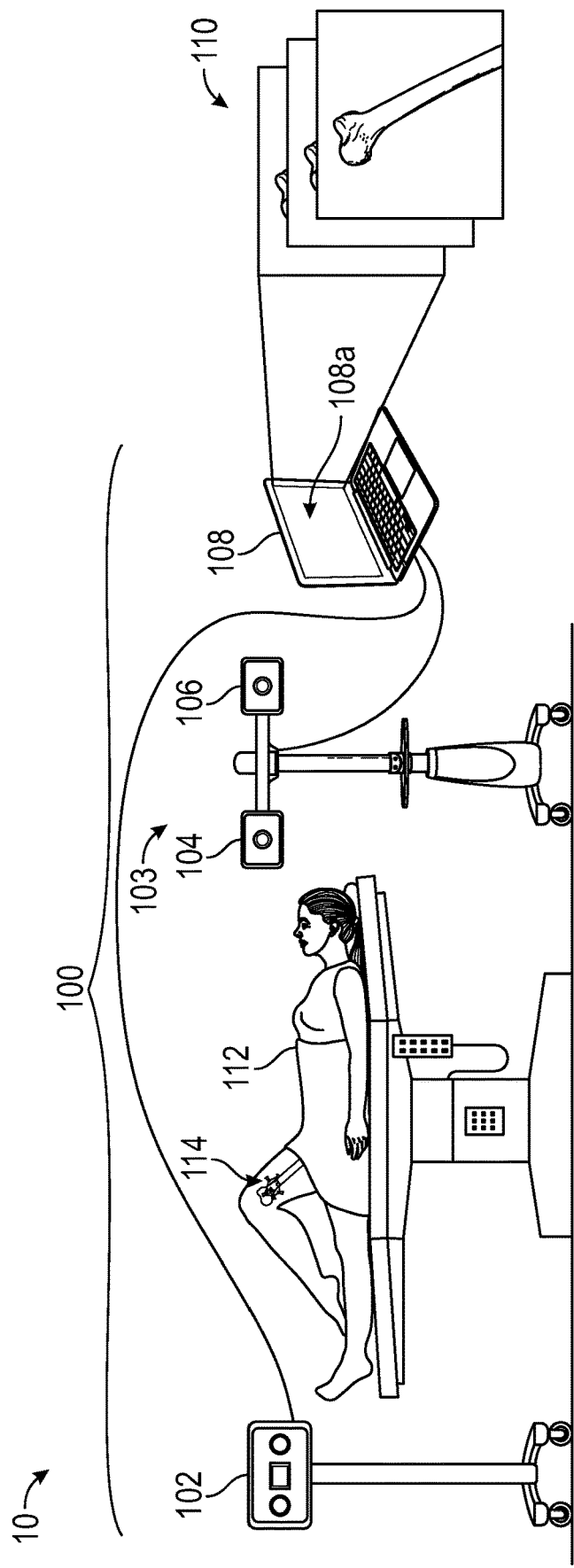
FIG. 1 is a diagram illustrating an example of an environment in which a surgical system may be used in accordance with the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Disclosed herein is a surgical system. Recreating preoperative surgical plans during surgery can be very difficult. For example, making a precise bone cut along a plane determined preoperatively on a CT scan image can be very difficult. Surgeons can use visible or palpable landmarks, rulers, and/or mechanical jigs at the time of surgery to help recreate the preoperative plan. However, these simple methods frequently result in inaccurate bone cuts. During surgery, it can be very difficult to visualize landmarks and accurately make precise bone cuts, even with mechanical jigs that may or may not be placed in the proper position.

The present surgical system can be utilized to assist surgeons with accurately and precisely recreating preoperative surgical plans during surgery. In at least one example, a marker coupled with the bone can be registered to the bone in a controller. The marker can include a three-dimensional body. At least a portion of the three-dimensional body and at least a portion of the bone can be scanned by a three-dimensional scanner to form a bone scan. The bone scan can be brought closer to and/or together with a bone image obtained preoperatively, such as a CT scan image. Accordingly, the marker and the bone can be registered more accurately and simpler than conventional methods. For example, some conventional systems require a surgeon to use a hand probe to touch the surface of bone dozens of times to manually generate a point cloud which can take time, is cumbersome, and, due to the relatively limited amount of data points obtainable by this method, can create significant inaccuracies in registration. Another conventional way to register a marker may be to obtain CT or X-rays during the surgical procedure after the marker is placed on the bone which can be expensive, require the use of large equipment, and unnecessarily expose the patient and hospital staff to radiation.

In some examples, the surgical system tracks the movement of the bone to accurately and precisely project light to guide the surgeon during surgery. For example, the light may include a cutting line to indicate the cutting point and/or plane for the surgeon to cut the bone during surgery. In some examples, the surgical system may track the movement of the bone by the use of a tracking component of the marker. For example, the tracking component may include a two-dimensional pattern and/or reflecting tracking features to be scanned by a camera and recognized by the controller. The position of the tracking component in relation to the bone and/or the registration component can be predetermined and/or known by the controller. Accordingly, once the bone is registered, the controller is able to track the movement of the tracking component and correspondingly track the movement of the bone in real-time.

In at least one example, one or more jigs can be utilized to guide the surgical blade during bone cuts. The components, orientation, and/or shape of jigs readily available to the surgeon can be stored in the memory of the controller. Accordingly, the surgeon can prepare a preoperative plan and determine the jig and/or make-up of the jig needed during surgery. The surgeon can then easily obtain and utilize the correct jig for surgery. For example, a modular jig may be created out of modular components. The bone cut may include an irregular shaped cut, and a specific shaped jig may be needed. The controller may be utilized to determine which modular components readily available can be combined and/or modified during preoperative planning. The surgeon and/or surgery staff can then create the modular jig without the need for conventional 3D printed custom jigs which can still result in substantial inaccuracies due to challenges in jig placement on the bone during surgery. Furthermore, conventional methods of producing custom jigs are very expensive and can take a significant time to generate-sometimes days or weeks; even after such cost and effort, the jig is single use and has to be discarded after just one surgery.

To ensure the accurate and precise placement of the jig, the jig may include alignment markers. The projector can then project light that includes alignment lines to correspond with the alignment markers. Accordingly, the jig simply needs to be positioned such that the alignment lines are aligned with the alignment markers.

As the surgical system is tracking the movement of the bone in real-time, the projected light such as the cutting line and/or the alignment lines may be adjusted in real-time to correspond with the movement of the bone. Accordingly, the preoperative surgical plan can be accurately recreated during surgery.

The disclosure now turns to FIG. 1, which illustrates a diagrammatic view of an exemplary surgical environment 10 for a surgical system 100, in which the present disclosure may be implemented. As illustrated in FIG. 1, a surgical system 100 can include a controller 108, a 3D surface scanner 102 communicatively coupled with the controller 108, and a projector system 103 communicatively coupled with the controller 108. The surgical system 100 may be utilized during surgery on a patient 112. The patient 112, as illustrated in FIG. 1, has an exposed bone surface 114 as the patient 112 is undergoing bone surgery such as a total knee arthroplasty which can include distal femur and proximal tibia cuts of the bone, total hip arthroplasty which can include femoral neck osteotomy, a tumor resection which can include custom, patient-specific cuts of bone to ensure removal of tumor, and/or procedures where specific placement of a screw, pin, and/or needle is required or skeletal deformity correction surgery.

The 3D surface scanner 102 is operable to optically scan an object, for example a bone, a marker, a mold, or any other surface. The 3D surface scanner 102 transmits the scan of the object to the controller 108 which can then process the digitally scanned surface of the object. The 3D surface scanner 102 can include, for example, a structured light projector and one or more cameras. An example of the 3D surface scanner 102 can be EinScan-SP.

As illustrated in FIG. 1, the 3D surface scanner 102 may be fixably attached to a rolling stand and brought into range of exposed bone surface 114 of patient 112 as required. In some examples, the 3D surface scanner 102 may be fixably attached at a location in the operating room such that is in range of exposed bone surface 114 of patient 112. In some examples, the 3D surface scanner 102 may be disposed on a pivoting and/or swivelling arm which can, for example, be coupled to the ceiling or a mounting system above the patient 112.

In at least one example, during operation, the projector of the 3D surface scanner 102 can project structured light pattern onto the target of the object, such as the exposed bone surface 114. The cameras capture the distorted pattern of the structured light on the target. Based on the image with distorted structured light pattern, the 3D surface scanner 102 can capture a 3D scanned surface, and the controller 108 can digitally construct the 3D scanned surface using a computer algorithm. In some examples, each scan can take about 30-60 seconds. In some examples, each scan may take less than 30 seconds, for example substantially instantaneously.

The projector system 103 can include a camera 104 and a projector 106. The camera 104 is operable to capture images and/or video. For example, the camera 104 can include an 8MP 5-50 mm Varifocal Lens USB Camera with a Sony IMX179 Sensor. The projector 106 can project an array of desired patterns and/or colors onto a surface. For example, the projector 106 can include a BenQ TK800 projector. The camera 104 and the projector 106 have a predetermined fixed relative position to each other. For example, as illustrated in FIG. 1, the camera 104 and the projector 106 are disposed on the same stand or frame. In some examples, the camera 104 and the projector 106 may be separated such that the camera 104 and the projector 106 can move independent from one another.

In at least one example, the projector system 103 can be calibrated prior to the surgery to obtain extrinsic parameters such as the relative position between camera 104 and projector 106 and to obtain intrinsic parameters of the camera 104 and/or the projector 106 such as lens focal length, lens distortion, and/or sensor pixel size. In at least one example, when projector system 103 is calibrated, the relative positions between the camera 104 and the projector 106 remain consistent and stable. In some examples, the projector system 103 can continuously calibrate the relative positions between the camera 104 and the projector 106 as each one may move independently from the other. For example, the camera 104 and/or the projector 106 may include sensors such as accelerometers and/or gyroscopes to sense positioning and/or movement of the camera 104 and/or the projector 106. Accordingly, when the camera 104 and/or the projector 106 move, the projector system 103 can re-calibrate the relative positions between the camera 104 and the projector 106.

In at least one example, as illustrated in FIG. 1, the projector system 103 may be fixably attached to a rolling stand and brought into range of exposed bone surface 114 and/or the desired surface to track and/or have an image projected thereon as required. In some examples, the projector system 103 may be fixably attached anywhere in operating room such that it is in range of exposed bone surface 114 as required. In some examples, the projector system 103 may be disposed on a pivoting and/or swivelling arm which can, for example, be coupled to the ceiling or a mounting system above the patient 112.

In at least one example, surgical systems 100 where the 3D surface scanner 102 and the projector system 103 are a single, fully integrated system are contemplated. Further, surgical systems 100 where a plurality of 3D surface scanners 102 are integrated with one or more cameras 104 and projectors 106 are also contemplated.

The controller 108 can include a monitor 108a that can be used to view images and/or video, for example, of exposed bone surface 114. In some examples, the images and/or videos displayed on monitor 108a can be captured in real-time by camera 104. In some examples, the monitor 108a may be used to display images and/or video, for example, of manuals, instructions, previous scans, or any other suitable information desired at the time of surgery. For example, preoperative images 110 may be displayed on the monitor 108a. Preoperative images 110 may be from any clinically relevant imaging modality a clinician may use such as images obtained during X-ray, CT scan, or MRI scan.

Figure 2:
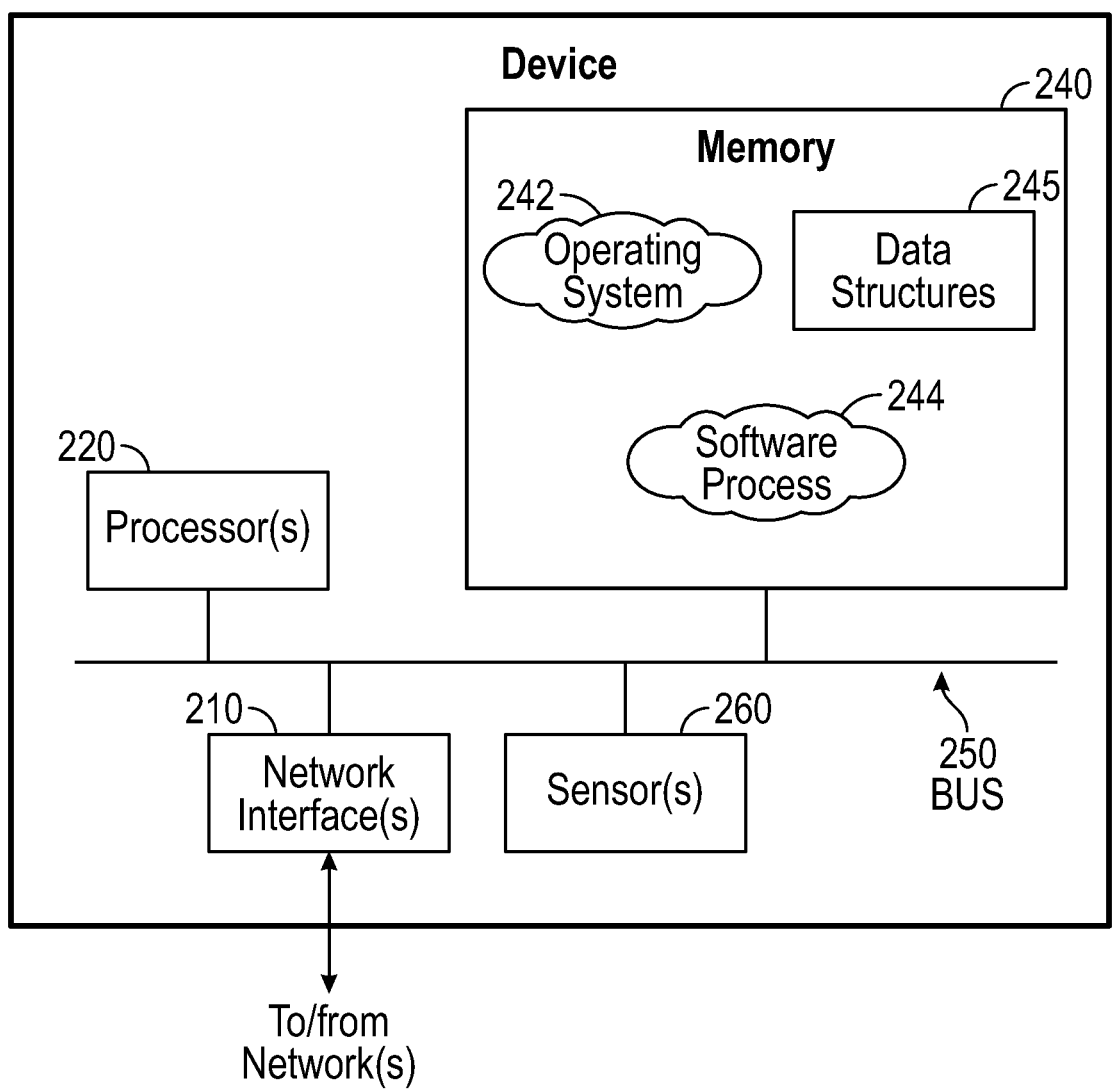
FIG. 2 is a diagram of a controller which may be employed as shown in FIG. 1.

FIG. 2 is a block diagram of an exemplary controller 108. Controller 108 is configured to perform processing of data and communicate with the surgical components, for example as illustrated in FIG. 1. In operation, controller 108 communicates with one or more of the above-discussed components and may also be configured to communication with remote devices/systems.

As shown, controller 108 includes hardware and software components such as network interfaces 210, at least one processor 220, sensors 260 and a memory 240 interconnected by a system bus 250. Network interface(s) 210 can include mechanical, electrical, and signaling circuitry for communicating data over communication links, which may include wired or wireless communication links. Network interfaces 210 are configured to transmit and/or receive data using a variety of different communication protocols, as will be understood by those skilled in the art.

Processor 220 represents a digital signal processor (e.g., a microprocessor, a microcontroller, or a fixed-logic processor, etc.) configured to execute instructions or logic to perform tasks in a surgical environment. Processor 220 may include a general purpose processor, special-purpose processor (where software instructions are incorporated into the processor), a state machine, application specific integrated circuit (ASIC), a programmable gate array (PGA) including a field PGA, an individual component, a distributed group of processors, and the like. Processor 220 typically operates in conjunction with shared or dedicated hardware, including but not limited to, hardware capable of executing software and hardware. For example, processor 220 may include elements or logic adapted to execute software programs and manipulate data structures 245, which may reside in memory 240.

Sensors 260 typically operate in conjunction with processor 220 to perform measurements, and can include special-purpose processors, detectors, transmitters, receivers, and the like. In this fashion, sensors 260 may include hardware/software for generating, transmitting, receiving, detection, logging, and/or sampling temperature, bone alignment, time, or other parameters.

Memory 240 comprises a plurality of storage locations that are addressable by processor 220 for storing software programs and data structures 245 associated with the embodiments described herein. An operating system 242, portions of which may be typically resident in memory 240 and executed by processor 220, functionally organizes the device by, inter alia, invoking operations in support of software processes and/or services 244 executing on controller 108. These software processes and/or services 244 may perform processing of data and communication with controller 108, as described herein. Note that while process/service 244 is shown in centralized memory 240, some examples provide for these processes/services to be operated in a distributed computing network.

It will be apparent to those skilled in the art that other processor and memory types, including various computer-readable media, may be used to store and execute program instructions pertaining to the surgical techniques described herein. Also, while the description illustrates various processes, it is expressly contemplated that various processes may be embodied as modules having portions of the process/service 244 encoded thereon. In this fashion, the program modules may be encoded in one or more tangible computer readable storage media for execution, such as with fixed logic or programmable logic (e.g., software/computer instructions executed by a processor, and any processor may be a programmable processor, programmable digital logic such as field programmable gate arrays or an ASIC that comprises fixed digital logic. In general, any process logic may be embodied in processor 220 or computer readable medium encoded with instructions for execution by processor 220 that, when executed by the processor, are operable to cause the processor to perform the functions described herein.

Figure 3:
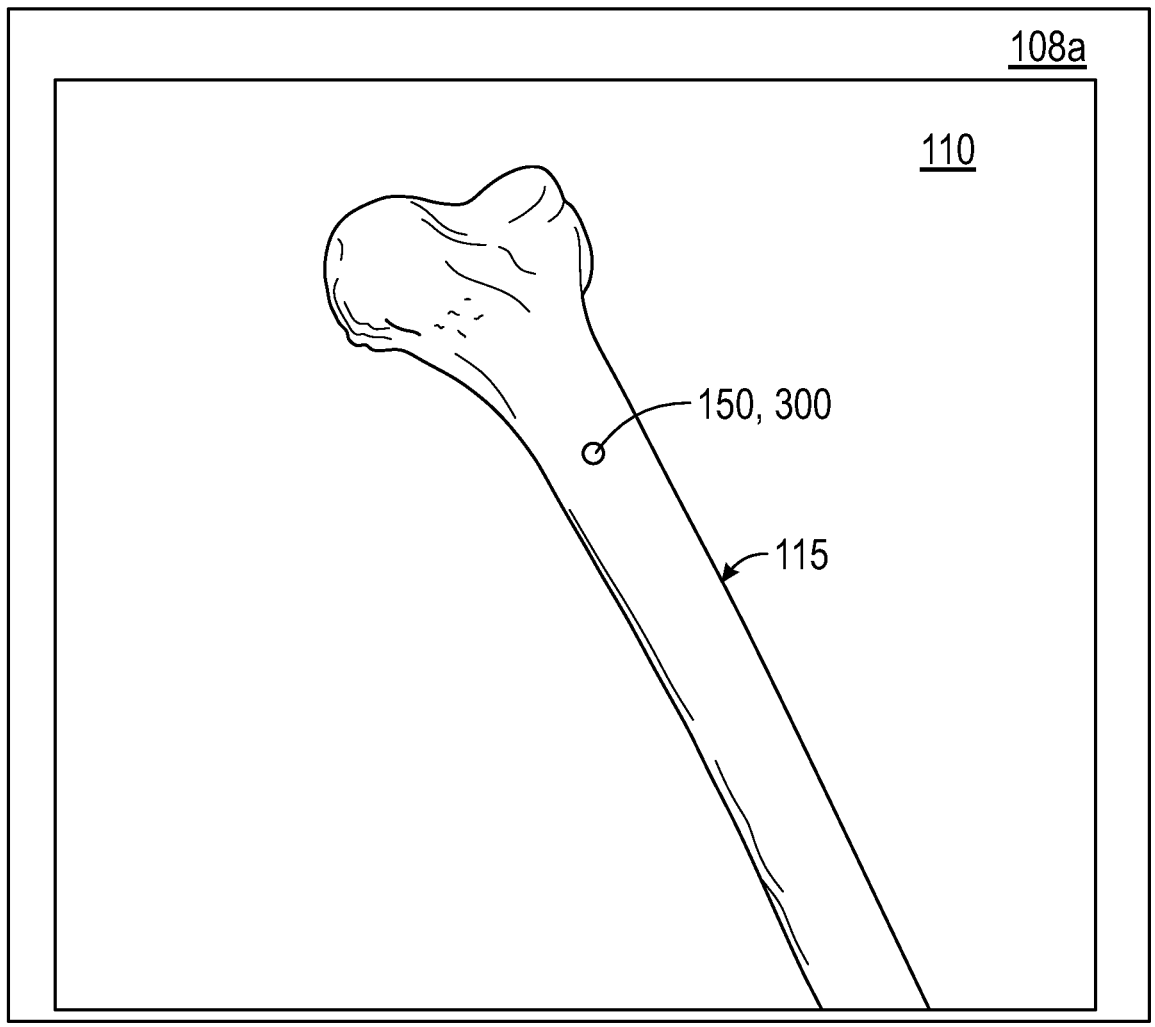
FIG. 3 is a diagram illustrating a preoperative plan being displayed from a controller.
Figure 4A:
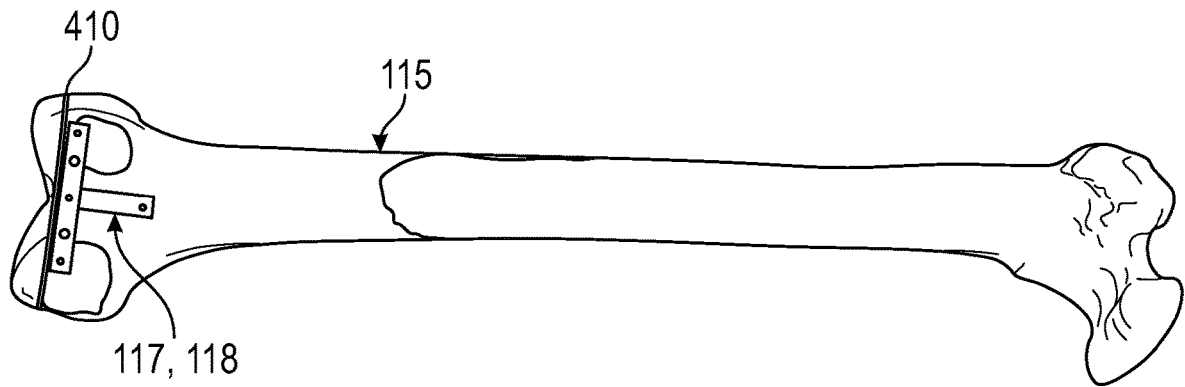
FIGS. 4A-4G are diagrams illustrating a preoperative plan being displayed from a controller using a linear jig.
Figure 4B:
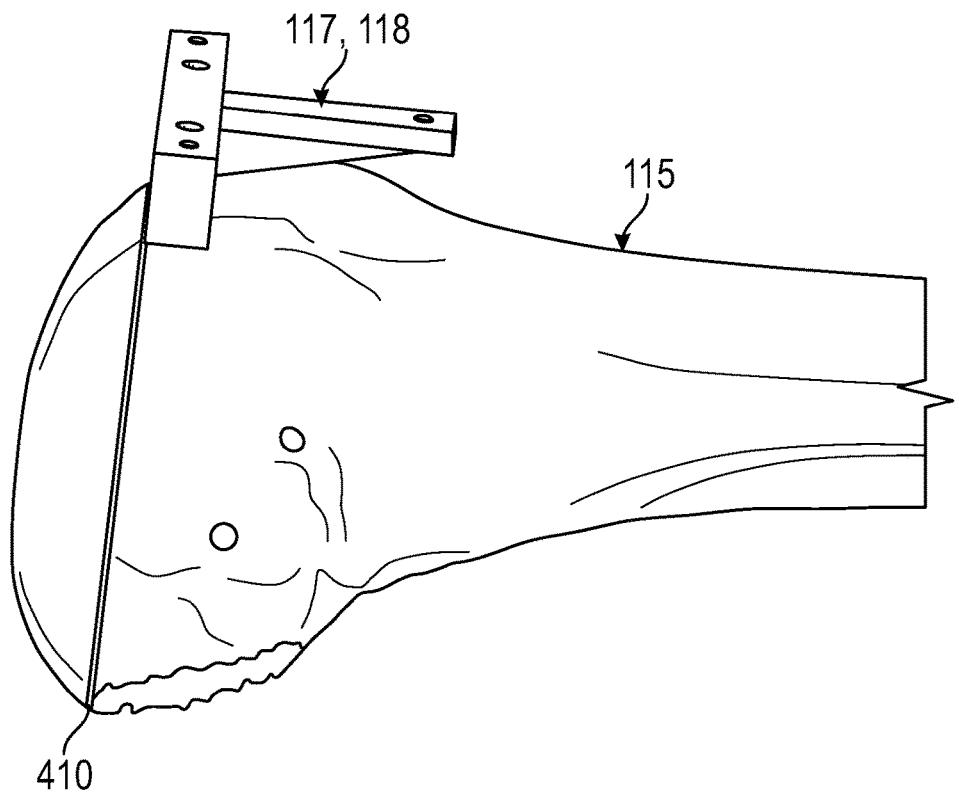
Figure 4C:
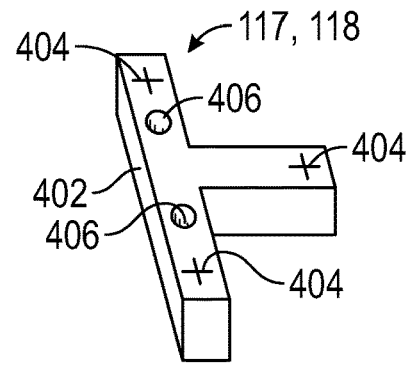
Figure 4D:
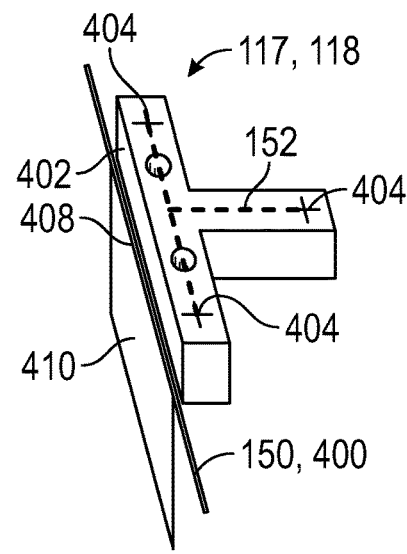
Figure 4E:
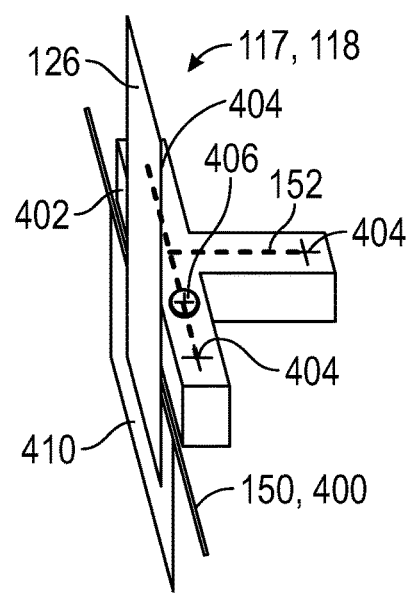
Figure 4F:
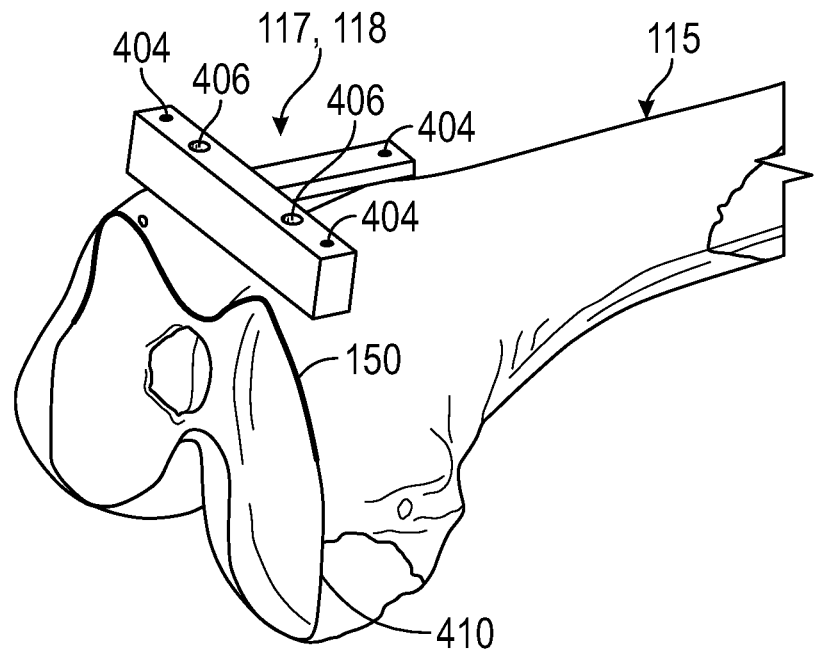
Figure 4G:
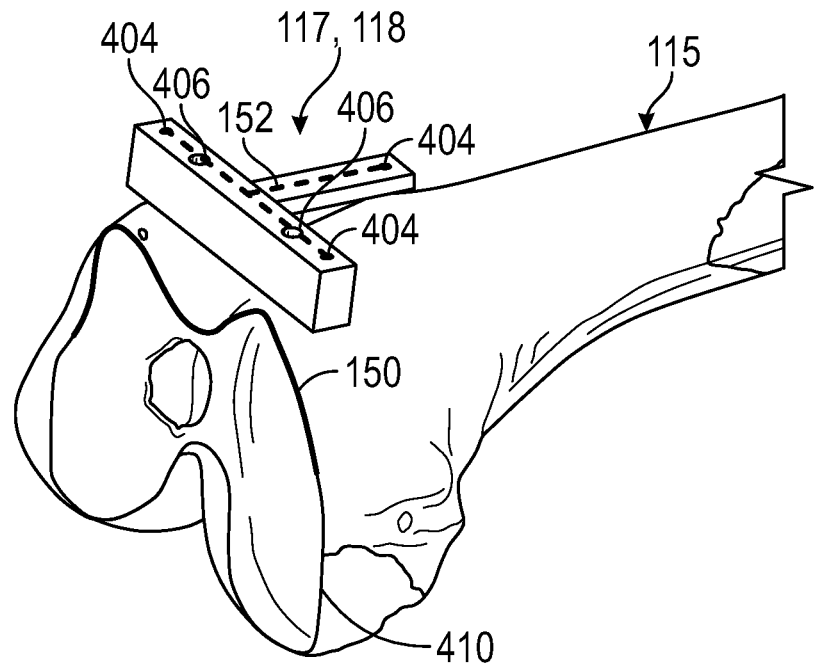
Figure 5A:
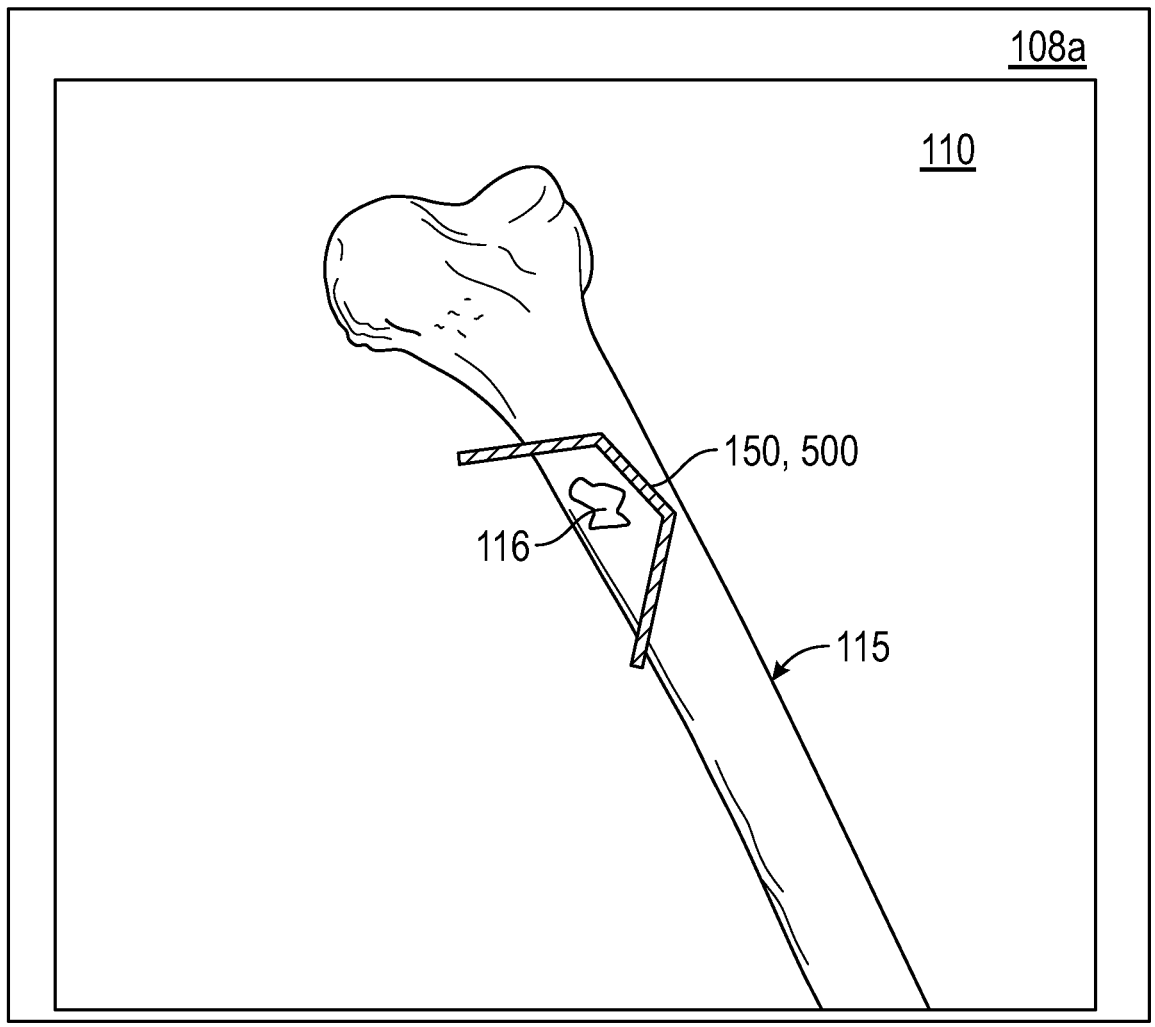
FIGS. 5A and 5B are diagrams illustrating a preoperative plan being displayed from a controller using a modular jig.
Figure 5B:
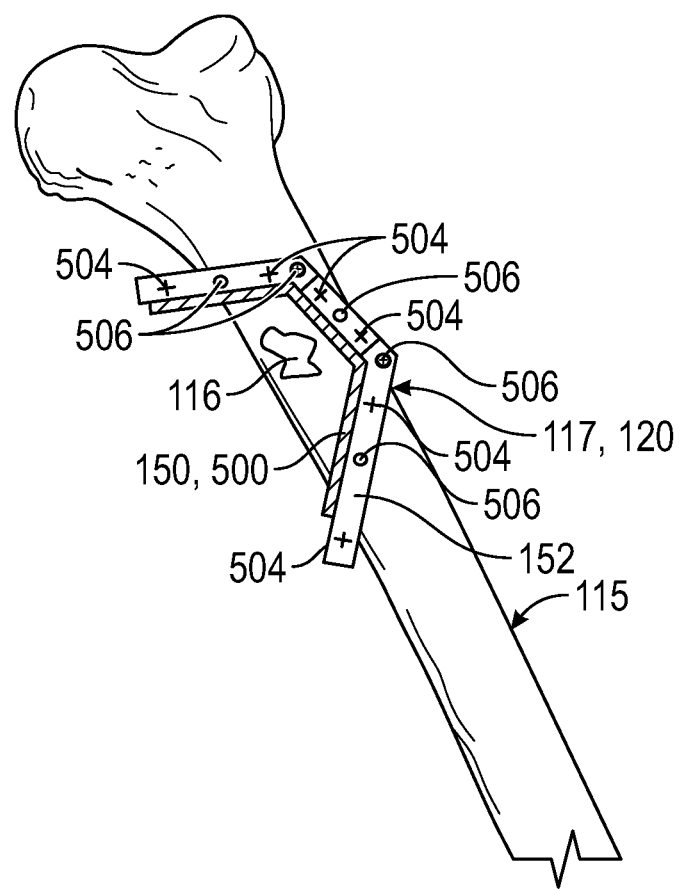

FIGS. 3-5B illustrate exemplary preoperative images 110 which may be displayed, for example, on a monitor 108a. During preoperative planning, the doctor is able to determine, using the controller 108, the actions required and desired during operation. The doctor can determine a cutting line 150 which can align with the desired cut or interaction with the exposed bone 114. However, during preoperative planning, in the preoperative image 110, the doctor can place the desired cutting line 150 on the bone image 115 in the preoperative image 110. In some examples, as illustrated in FIG. 3, the cutting line 150 can include a dot projection 300 which can indicate, for example, a point for a needle, pin, screw, and/or a puncture to be placed in the exposed bone 114. FIGS. 4A-4G illustrate examples of the cutting line 150 including a linear projection 400 along a cutting plane 410. FIGS. 5A and 5B illustrate examples of the cutting line 150 including an irregularly shaped projection 500. While the cutting lines 150 can be shown as substantially straight lines, the cutting line 150 can be shown as the intersection of a top curve line between the cutting plane 410 to the bone image 115. Accordingly, the cutting line 150 at certain viewing angles may appear straight while at other viewing angles may appear curved to follow the curvature of the bone 114, 115. In some examples, the cutting line 150 and subsequent projection can be any line, dot, circle, rectangle, triangle, and/or any shape as clinically desired.

FIGS. 4A-4G illustrate exemplary preoperative images 110 which may be displayed during preoperative planning for a linear cut of the bone 114. FIG. 4A illustrates a cutting plane 410 which correlates to the desired cut to be made during the operation. For example, the cutting plane 410 correlates with the cutting path of a surgical blade such as a saw blade to cut the bone in the proper location and angle. As illustrated in FIGS. 4A and 4B, the cutting plane 410 may correlate with a cut in a femur during a total knee arthroplasty.

To ensure proper alignment and provide a stable cut by the surgical blade, a jig 117 can be used. FIGS. 4A-6 illustrated exemplary uses of different jigs 117 to guide a surgical blade during operation. The jig 117 can provide a surface for which the surgical blade can abut such that the jig 117 guides the blade during the cutting process.

The jig 117 can include a linear jig 118 which, as illustrated in FIGS. 4A-4G, can be formed in the shape of a T. As illustrated in FIG. 4C, the linear jig 118 includes one or more coupling components 406 which are operable to couple the linear jig 118 with the bone 114 such that the linear jig 118 does not move and become misaligned. For example, the coupling components 406 can include recesses operable to receive couplers such as screws to couple the linear jig 118 with the bone 114. In some examples, the coupling components 406 can include one or more straps, a secondary element intermediate the jig 117 with the bone 114, or any other suitable component to couple the jig 117 with the bone 114.

As illustrated in FIGS. 4C and 4D, the linear jig 118 has a blade surface 402 which is aligned with the linear cutting plane 410 to serve as a guide to the surgical blade. The blade surface 402 of the linear jig 118 provides a linear surface to guide the blade for a linear cut. In other examples, the linear jig 118 can be any shape such that the linear jig 118 provides a guide surface for a linear cutting plane 410, such as rectangular, triangular, or any other suitable shape. Additionally, in some examples, the linear jig 118 can include different configurations for guiding the surgical blade along the cutting plane 410. For example, the linear jig 118 can include a linear aperture for which the surgical blade is inserted through ensure a stable and straight cut in the bone 114.

During preoperative planning on the controller 108, the positioning of an alignment line 152 and/or a cutting line 150 can be determined. As illustrated in FIG. 4D, the controller 108 can determine the positioning of an alignment line 152. The alignment line 152 includes light which can be projected during operation to indicate the precise alignment of the linear jig 118. In at least one example, the linear jig 118 can include a plurality of alignment markers 404 which are operable to ensure the correct and precise alignment of the linear jig 118. When the alignment line 152 is aligned with the alignment markers 404, for example as illustrated in FIGS. 4D and 4E, the linear jig 118 is accurately and precisely positioned. The cutting plane 410 and blade surface 402 of the linear jig 118 are also accurately and precisely aligned.

In at least one example, as illustrated in FIGS. 4D and 4E, the controller 108 can determine the positioning of a cutting line 150 which includes light emitted on the bone surface 114 to ensure the alignment of the cutting surface 402 and the cutting plane 410. As illustrated in FIGS. 4D and 4E, the cutting line 150 can include a linear cutting line 400. When the linear jig 118 is adequately positioned such that the cutting surface 402 is aligned with the cutting plane 410 along the cutting projection, as illustrated in FIG. 4E, the surgical blade 126 can then make a surgical cut with known parameters, for example cutting through cutting plane 410 and entering the bone surface 114 through cutting plane 410, allowing for accurate implementation of the preoperative surgical plan.

As illustrated in FIGS. 4F and 4G, the preoperative planning can include a simulation of the positioning of the linear jig 118 on the bone image 115, for example, with the alignment line 152. Additionally, FIGS. 4F and 4G illustrate the bone image 115 after a simulated cut has been made along the cutting plane 410 to determine whether a cut along the cutting plane 410 produces the desired bone cut to achieve the desired clinical results.

FIG. 5A illustrates an exemplary preoperative plan where the desired projection line 150 is an irregularly shaped projection line 500 to indicate the desired cutting path and/or cutting plane of the bone. For example, as illustrated in FIG. 5A, a tumor 116 may need to be resected, and the projection line 500 needs to have three lines cut along different angles to surround the tumor 116. FIG. 5B illustrates the use of a jig 117 to guide a surgical blade along the cutting path and/or cutting plane and projection line 500. As the determined path along the projection line 500 is not a single linear path, a modular jig 120 can be utilized. The modular jig 120 is similar to the linear jig 108 of FIGS. 4A-4G, however the modular jig 120 can be modified to fit along a linear and/or non-linear projection line 500 and cutting path and/or cutting plane.

In at least one example, similar to the linear jig 108, the modular jig 120 can include a plurality of alignment markers 504 which are operable to ensure the correct and precise alignment of the modular jig 120. When the alignment line 152 is aligned with the alignment markers 504, for example as illustrated in FIG. 5B, the modular jig 120 is accurately and precisely positioned. The cutting plane and blade surface of the modular jig 120 are also accurately and precisely aligned to execute the precise bone cut as determined in the preoperative plan.

As illustrated in FIG. 5B, the modular jig 120 includes one or more coupling components 506 which are operable to couple the modular jig 120 with the bone 114 such that the modular jig 120 does not move and become misaligned. For example, the coupling components 506 can include recesses operable to receive couplers such as screws to couple the modular jig 120 with the bone 114.

Figure 5C:
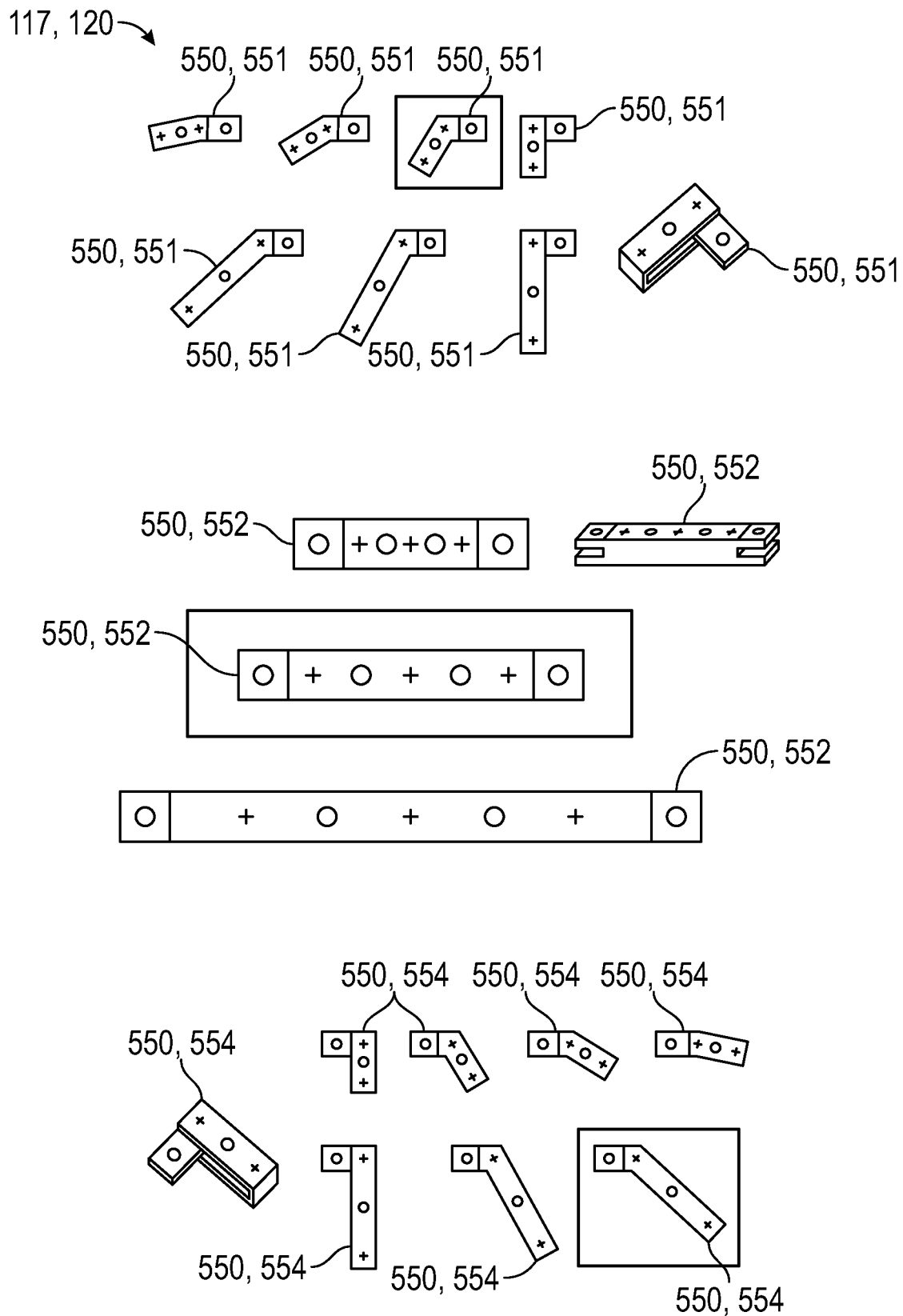
FIG. 5C are diagrams illustrating exemplary modular pieces which can be used to create a modular jig.

As illustrated in FIG. 5C, the modular jig 120 can be composed of a number of different modular pieces 550. The modular pieces 550 can each have any predetermined size, shape, and/or design. For example, the modular pieces 550 can include a plurality of left pieces 551 having different sizes and angles. The plurality of left pieces 551 as illustrated in FIG. 5C can include at least one bend or curve. A plurality of central pieces 552 can be, for example, linear pieces, and a plurality of right pieces 554 can include at least one bend or curve. The left pieces 551 and the right pieces 554 can be configured to be coupled to each end of the central pieces 552. Any combination of modular pieces 550 can be linked together to form a modular jig 120 that fits the desired cutting path and/or cutting plane.

Figure 5D:
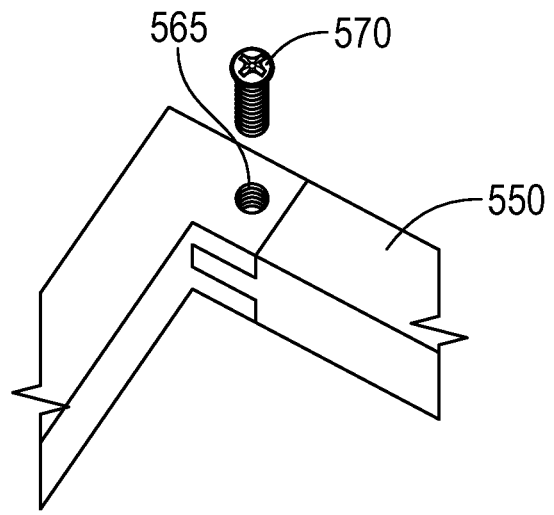
FIG. 5D is a diagram illustrating an exemplary coupling mechanism for modular pieces.
Figure 5D:
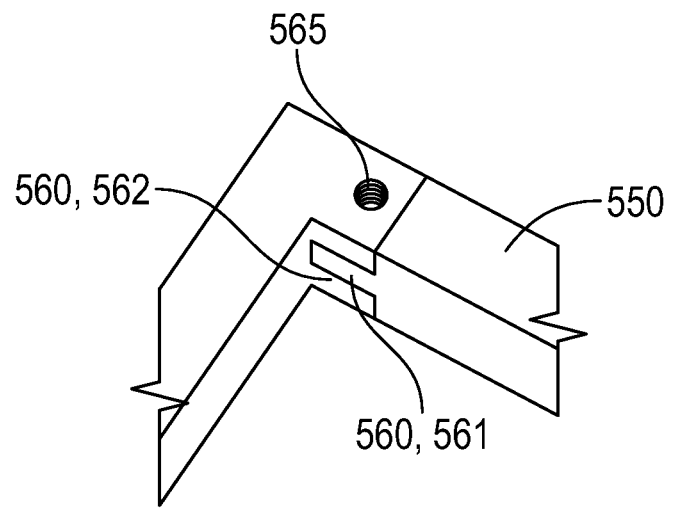
Figure 5D:
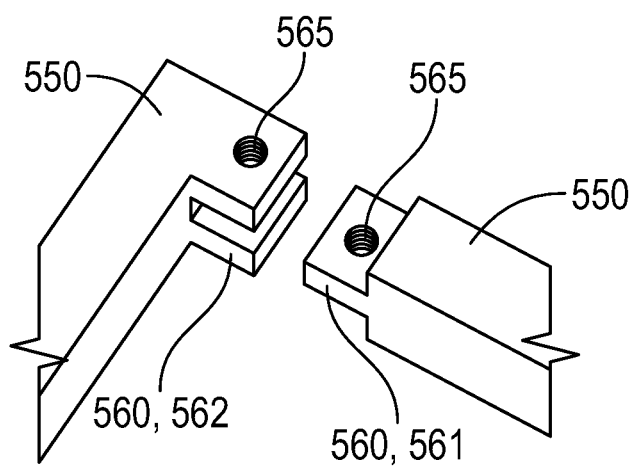

In at least one example, as illustrated in FIG. 5D, modular pieces 550 can be coupled to one another by coupling portions 560, for example using a fastener 570 such as a screw. A coupling portion 560 of one modular piece 550 can include a male portion 561 while another modular piece 550 can include a female portion 562 operable to receive the male portion 561. Both of the coupling portions 560 of the modular pieces 550 include fastening apertures 565 aligned with one another and operable to receive a fastener 570 such as a screw, a bolt, a magnet, or any other suitable fastener 570 to couple the modular pieces 550 together. In some examples, different coupling mechanisms can be utilized such that the modular pieces 550 are coupled together and maintain the shape of the modular jig 120.

Figure 5E:
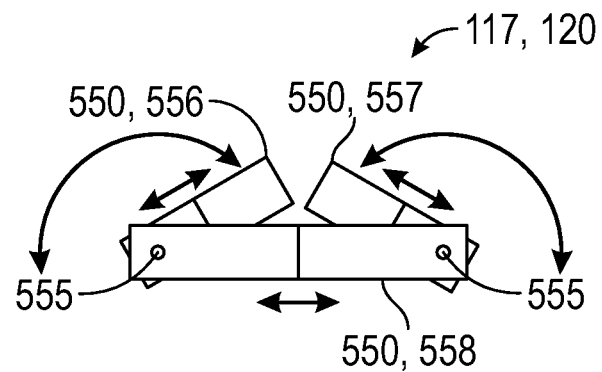
FIGS. 5E-5G are diagrams illustrating an exemplary modular jig where the modular pieces are extendable, rotatable, and/or retractable.
Figure 5F:
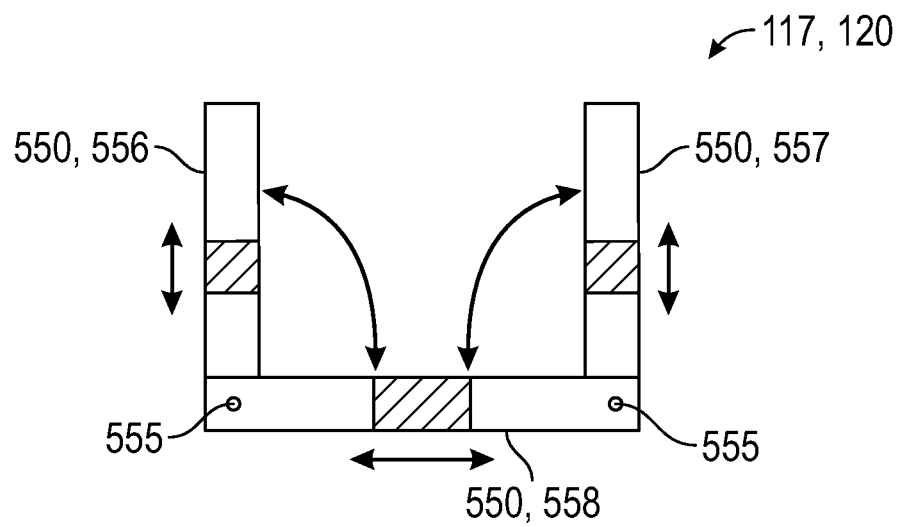
Figure 5G:
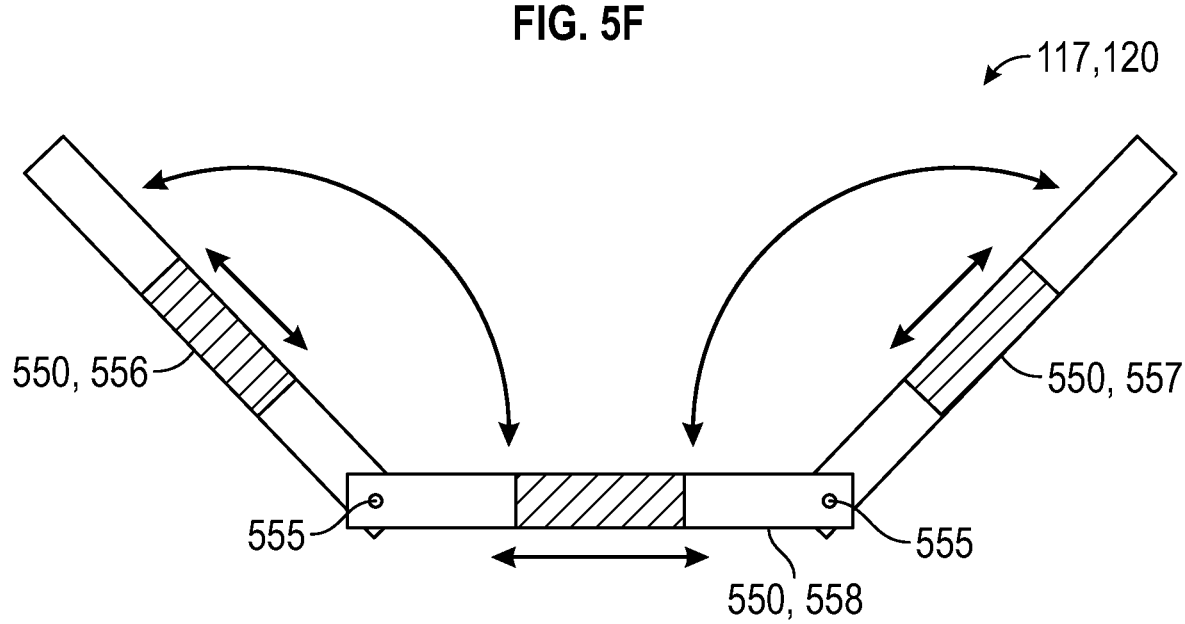

FIGS. 5E-5G illustrates examples of a modular jig 120 in which the modular pieces 550 can be pivoted in relation to one another, extended in length, and/or retracted in length. In at least one example, the precise angles and/or lengths of the modular pieces 550 of the modular jig 120 after pivoting and lengthening or retraction can be known by users, for example, by visualizing outputs of angles and lengths on modular jig 120. In at least one example, the precise angles and/or lengths of the modular pieces 550 of the modular jig 120 can be stored in memory of the controller 108. For example, the controller 108 may record wirelessly the angles and lengths through sensors or optical scanning. In some examples, the modular jig 120 may include sensors that measure the lengths and/or angles of the modular pieces 550 of the modular jig 120, and the sensors may transmit the measurements to the controller 108. Accordingly, as in the examples illustrated in FIG. 5E-5G, the modular jig 120 can be further customizable and adaptable to address any number of surgical cuts.

In at least one example, the controller 108 can store each modular piece 550 available to the surgical team. After the cutting line 150 and/or the alignment line 152 is determined, the controller 108 can determine the exact size and/or shape of the modular jig 120 needed by the surgical team. Additionally, in some examples, the controller 108 can construct, in preoperative planning, a modular jig 120 using the known modular pieces 550 available to the surgical team. With the preoperative plan, the surgical team can then easily pick out the modular pieces 550 identified by the controller 108 and construct or adjust the modular jig 120 exactly as determined in the preoperative plan. In another example, modular jig 120 illustrated in FIG. 5E-5G can be configured to the precise angles and lengths required for the preoperative plan by controller 108 by wired/wirelessly actuating modular jig 120 into configuration. For example, the modular jig 120 may include one or more motors which are operable to move the modular pieces 550 to the precise angles and/or lengths as directed by the controller 108. The surgical team does not then have to wait for a customized jig 117 to be created by a fabrication company, and can easily create any jig 117 without delay.

Figure 6:
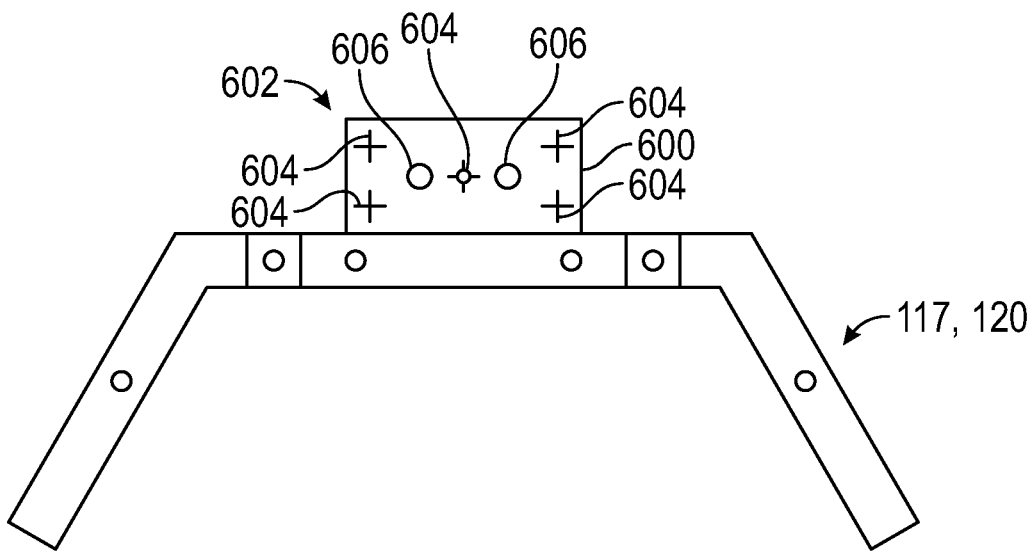
FIG. 6 is a diagram illustrating a jig with an exemplary alignment base.

FIG. 6 illustrates an exemplary alignment base 602 operable to ensure the correct and precise alignment of the jig 117. The alignment base 602 is operable to be coupled with a jig 117, for example modular jig 120, to ensure the alignment of the jig 117. Alignment of alignment base 602 may create corresponding alignment of jig 117 which can be coupled to alignment base 602, thereby eliminating the necessity of alignment markers 604 directly on jig 117. However, in at least one example, the jig 117 may still include alignment markers 604.

The alignment base 602 includes a plurality of alignment markers 604 which are operable to correspond with an alignment line 152. When the alignment line 152 is aligned with the alignment markers 604, the alignment base 602 is accurately and precisely positioned. Subsequently, the cutting plane and blade surface of the jig 117 are also accurately and precisely aligned.

The alignment base 602 can include one or more coupling components 606 which are operable to couple the alignment base 602 with the bone 114 such that the alignment base 602 does not move and become misaligned. For example, the coupling components 606 can include recesses operable to receive couplers such as screws to couple the alignment base 602 with the bone 114.

In at least one example, during preoperative planning, the controller 108 has stored in memory the available jigs 117, such as the linear jig 118, the modular jig 120 and/or the modular pieces 550 available to create the modular jig 120, and/or the alignment base 602. Accordingly, the required jig 117 can be determined and/or created in the controller 108 during preoperative planning such that the exact jig 117 and/or alignment base 602 can be utilized and/or recreated during surgery.

Figure 7A:
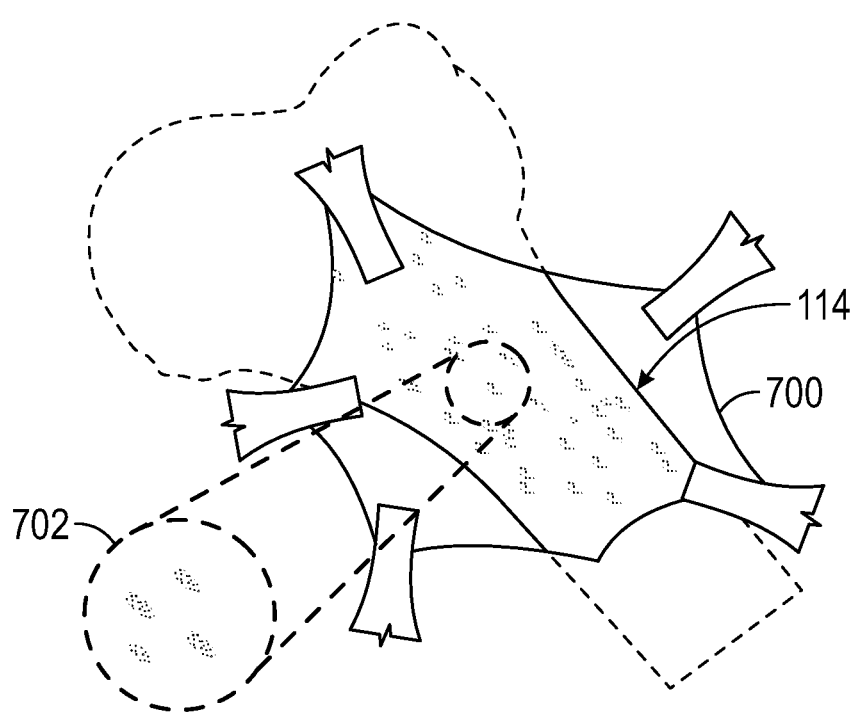
FIGS. 7A-7D are diagrams illustrating preparation of a bone surface to attach a marker.
Figure 7B:
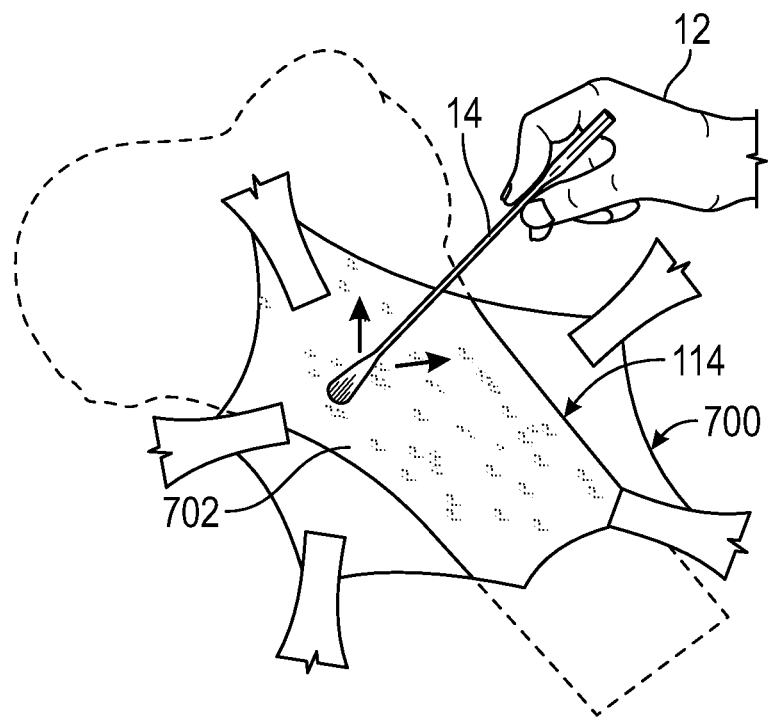
Figure 7C:
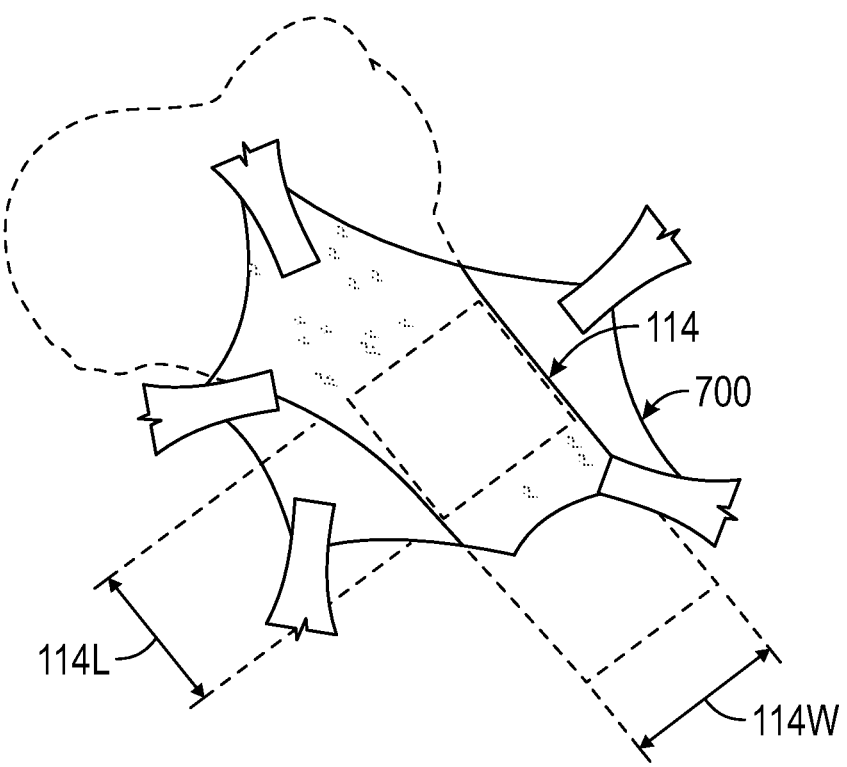

FIGS. 7A-7C illustrate steps during preparation of the bone 114 for surgery. As illustrated in FIG. 7A, the soft tissue 700 such as skin and muscle are dissected and pulled back to expose the bone 114. In some examples, residue small tissue 702 may remain on the surface of the bone 114. As illustrated in FIG. 7B, the surgeon 12 may utilize a tool 14 to cut the residue small tissue 702 from the surface of the bone 114. In some examples, as illustrated in FIG. 7B, the tool 14 may include an instrument such as a Cobb surgical instrument, however, any clinically acceptable method to remove tissue and expose bone surface may be used. As illustrated in FIG. 7C, the bone 114 is exposed and an area is cleaned of excess tissue. For example, the area of the exposed bone 114 may have a width 114W of about 3 centimeters and a length 114L of about 3 centimeters. The dimensions of the area of exposed bone 114 may vary as desired or needed for the surgery, or as needed by 3D surface scanner 102 to obtain enough information to execute accurate surface matching to preoperative images.

Figure 7D:
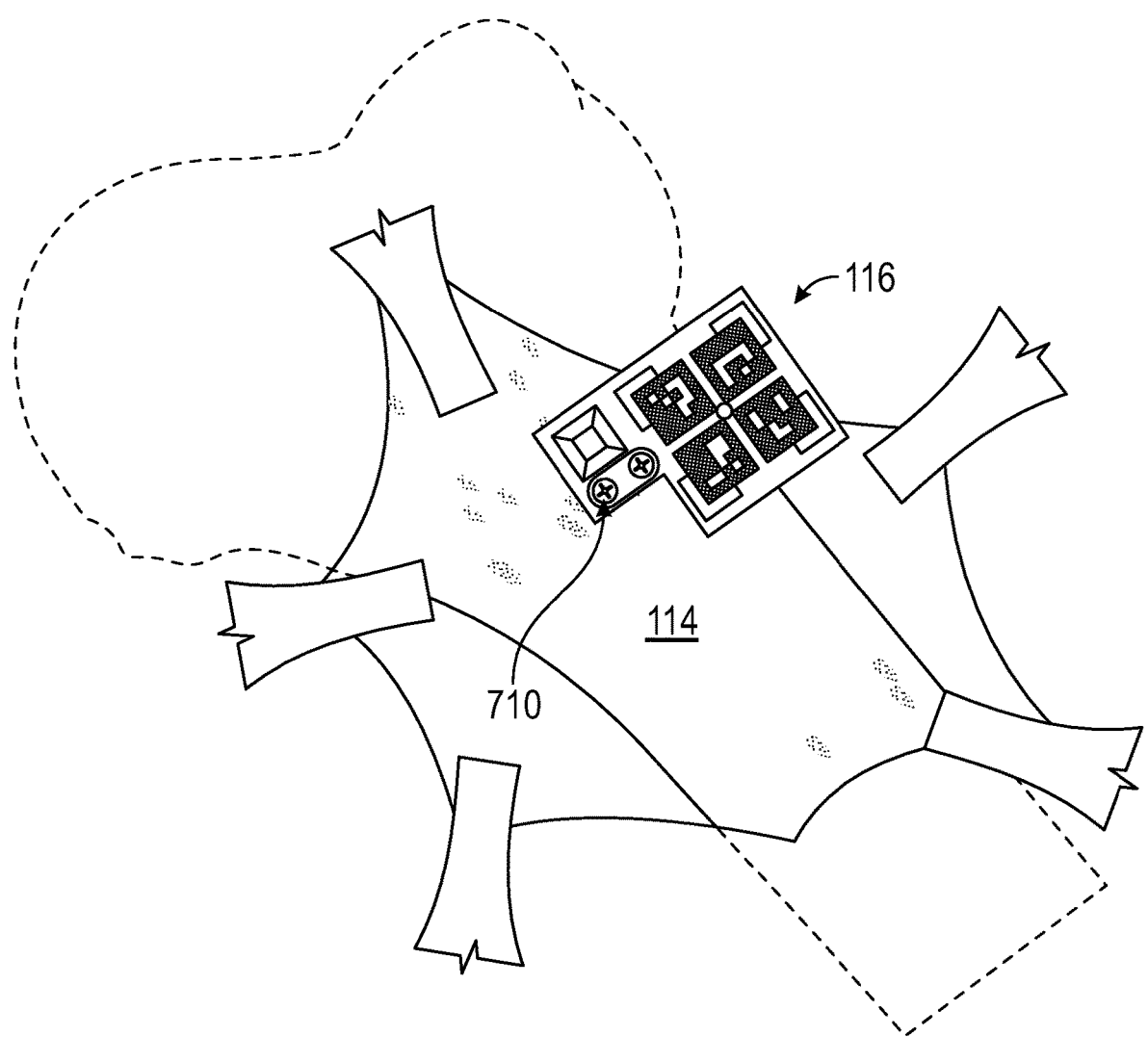

After the bone 114 is exposed, as illustrated in FIG. 7D, a marker 116 can be coupled to the bone 114. In some examples, as illustrated in FIG. 7D, the marker 116 can be directly coupled with the bone 114 by fasteners 710 such as screws, pins, or any other clinically acceptable device used for fixation to bone 114. In some examples, the marker 116 can be indirectly coupled with the bone 114 such that the marker 116 is coupled with another component or device in which the another component or device is directly or indirectly coupled to the bone 114. The marker 116 is affixed to the bone 114 proximate to the target bone area where there is no tissue covering the bone 114. The marker 116 is utilized to register and track the orientation and movement of the bone 114 during surgery. In some examples, the marker 116 is operable to be scanned by a surgical system 100 (shown in FIG. 1) such as the 3D surface scanner 102 and/or camera 104 of the projector system 103. The surgical system 100 is operable to scan the marker 116 on the bone 114, register the marker 116 in the controller 108 in reference to the preoperative image 110, and/or track the movement of the marker 116 and correlate the movement of the marker 116 in reference to the movement of the bone 114 during surgery. Additionally, with the understanding of the orientation and movement of the bone 114 due to the marker 116, the controller 108 can control the projector 106 of the projector system 103 to project light onto the bone 114 or one or more jigs 117 or corresponding components to align the jig 117 and subsequently accurately align the surgical blade to cut the bone 114.

FIGS. 8A-8D illustrate exemplary markers 116. The marker 116 can include a registration component 810 and a tracking component 850. The registration component 810 is operable to be scanned into a digital reproduction of at least a portion of the registration component 810 and at least a portion of the bone 114. Because the precise location of registration component 810 can be determined on bone 114 following surface extraction, the registration component 810 can provide data to the controller 108 regarding the precise location and/or orientation of the marker 116 in relation to the bone 114. The tracking component 850 is disposed a predetermined distance with a predetermined orientation in relation to the registration component 810 and is known by controller 108. The controller 108, upon registering the location and/or orientation of the registration component 810 through surface extraction the digital reproduction of the scan data to preoperative images, can then scan the tracking component 850, for example using the camera 104, to track the movement and/or orientation of the bone 114 in real time during surgery. For example, the tracking component 850 can include a 2-dimensional pattern 852 which can be scanned by the camera 104 and recognized by the controller 108 to track the movement of the tracking component 850. In some examples, the 2-dimensional pattern 852 can include a barcode, a QR code, or any other suitable pattern.

Figure 8A:
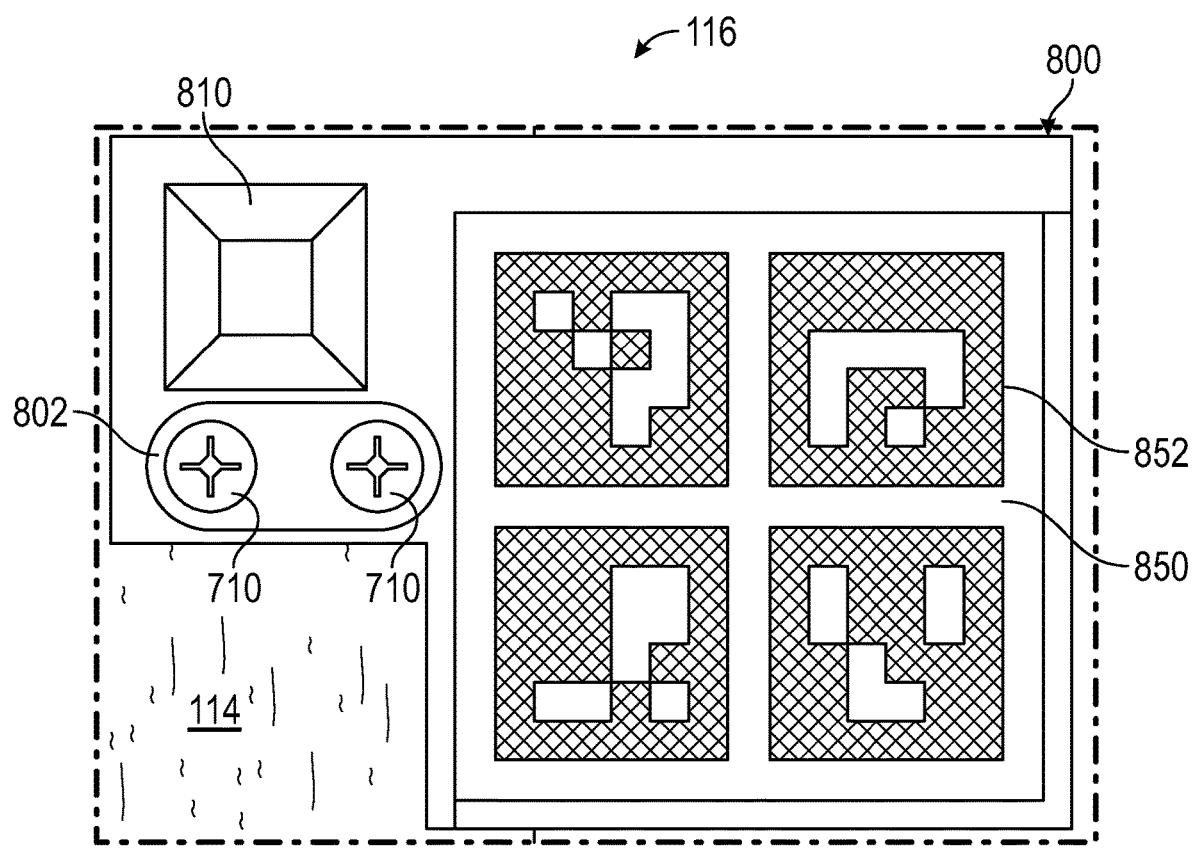
FIGS. 8A-8D are diagrams illustrating exemplary markers.
Figure 8B:
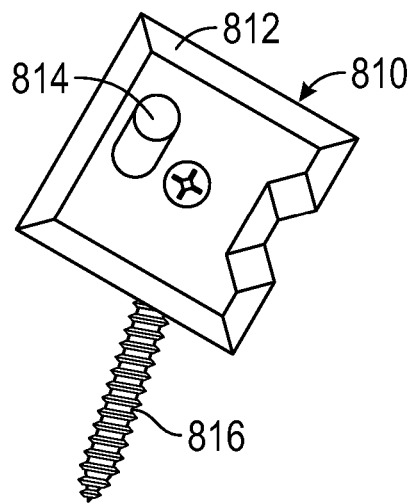

As illustrated in FIG. 8A, the registration component 810 and the tracking component 850 are disposed on one body 800. In some examples, the registration component 810 and the tracking component 850 can be separately provided. For example, FIG. 8B illustrates an exemplary registration component 810 which is a separate component from the tracking components 850 illustrated in FIGS. 8C and 8D. In some examples, the registration component 810 and the tracking component 850 can be configured to be coupled to one another. Even if separately provided, the distance and/or relationship between the registration component 810 and the tracking component 850 is predetermined and known. Accordingly, the controller 108 can track the tracking component 850 and subsequently the bone 114 during surgery with only a scan of at least a portion of the registration component 810 and at least a portion of the bone 114.

Figures 8C, 8D:
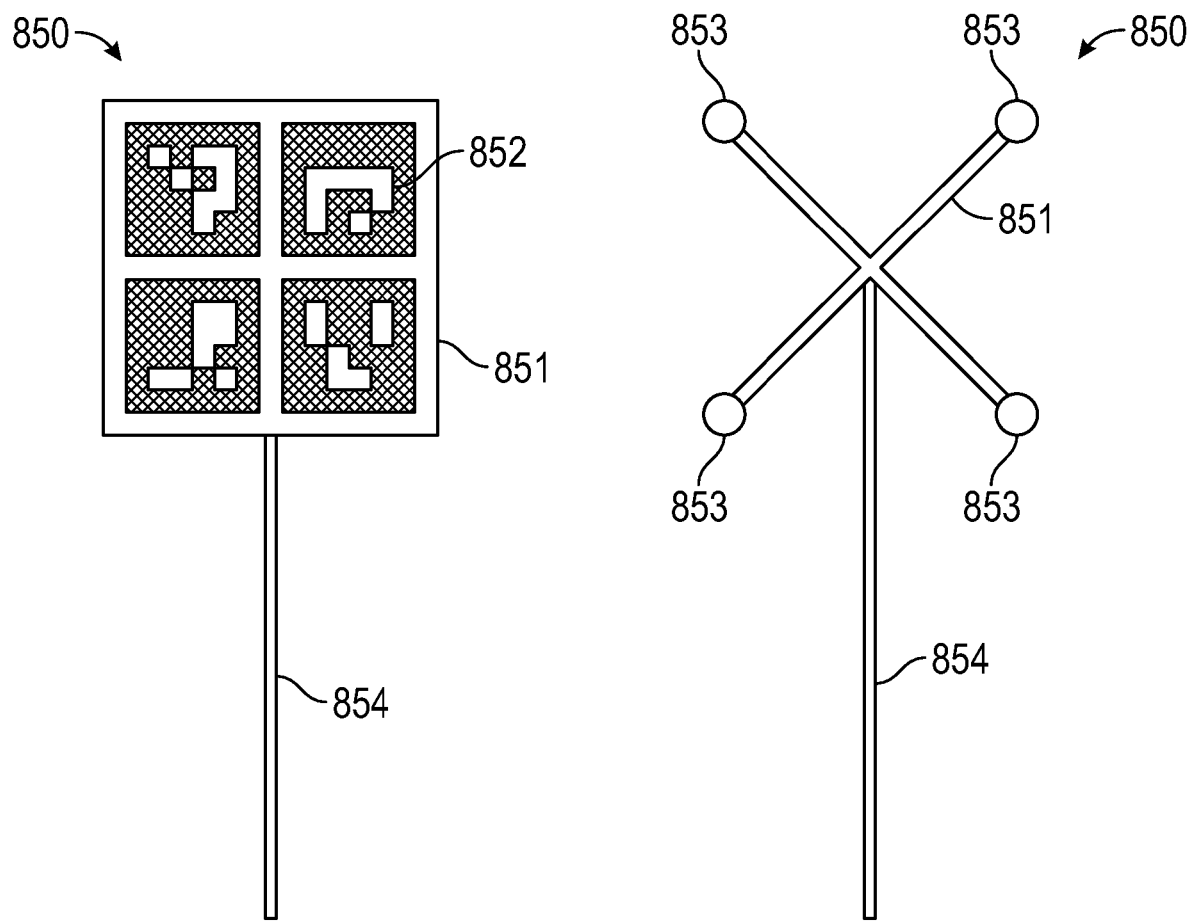

For example, as illustrated in FIGS. 8B-8D, the registration component 810 may include a three-dimensional body 812 which is operable to be scanned into the controller 108 to register the location and/or orientation of the marker 116 in relation to the bone 114. In at least one example, the registration component 810 can include a pin receiver 814 which is operable to receive a pin 854 or a corresponding coupling mechanism to couple the registration component 810 with the tracking component 850. The precise location of the registration component 810 to tracking component 850 can be precisely known. In some examples, the registration component 810 can include a bone fastener 816 such as a screw, a pin, or any other suitable fastener operable to couple the registration component 810 to the bone 114.

FIGS. 8C and 8D illustrate exemplary tracking components 850. The tracking components 850 are operable to be scanned, for example, by a camera 104 such that the controller 108 can track the movement of the tracking component 850 and subsequently the corresponding bone 114 in real time during surgery. As illustrated in FIGS. 8C, the tracking component 850, similar to FIG. 8A, can include a 2-dimensional pattern 852 such as a barcode, a QR code, or any other suitable pattern which can be scanned by the camera 104 and recognized by the controller 108 to track the movement of the tracking component 850. In some examples, as illustrated in FIG. 8D, the tracking component 850 can include one or more reflective tracking features 853 operable to be scanned by the camera 104 and recognized by the controller 108 to track the movement of the tracking component 850. The reflective tracking features 853 can be coated such that the reflective tracking features 853 shine when light is shone on the reflective tracking features 853.

In some examples, the reflective tracking features 853 may be tracked by the camera 104 which can be equipped with an infrared pass filter.

Figure 9:
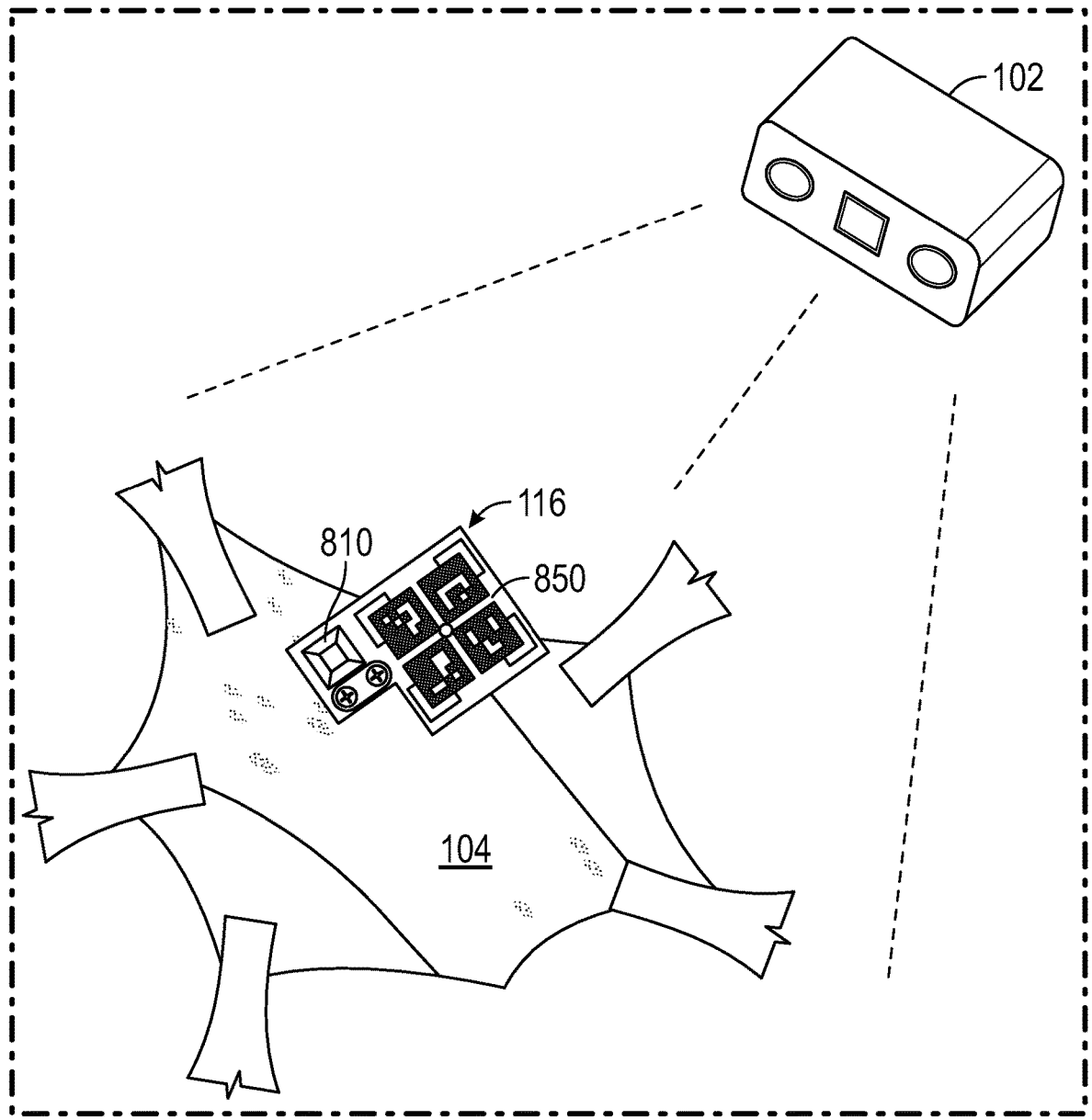
FIG. 9 is a diagram illustrating a marker and bone being scanned by a 3D surface scanner.

In at least one example, referring also to FIG. 9, at least a portion of the registration component 810 and at least a portion of the bone 114 can be scanned directly by the 3D surface scanner 102 to detect the location and/or orientation of the marker 116 in relation to the bone 114 in the controller 108. For example, as illustrated in FIG. 8A, the registration component 810 is substantially the shape of a flat-top 3-dimensional pyramid. In some examples, the registration component 810 can be any 3-dimensional shape that extends from the bone 114 such that the location as well as 3-dimensional orientation of the registration component 810 in relation to the bone 114 can be extracted. The controller 108 is operable to build a registration component 810 local coordinate on the bone 114.

Figure 10A:
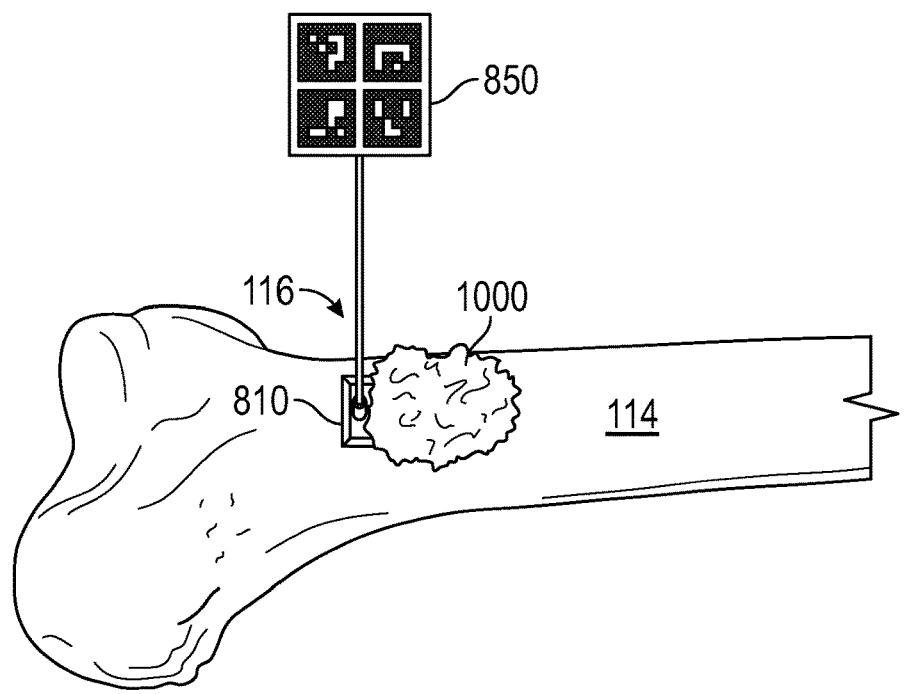
FIGS. 10A-10D are diagrams illustrating an impression material utilized to create an impression of at least a portion of a marker and bone to be scanned by a 3D surface scanner.

FIGS. 10A-10D illustrate a method to scan at least a portion of the registration component 810 and at least a portion of the bone 114 when the bone 114 is not readily or easily accessible to the 3D surface scanner 102. As illustrated in FIG. 10A, the marker 116 is coupled with the bone 114. An impression material 1000 is pressed against a portion of the bone 114 and at least a portion of the registration component 810 of the marker 116. The impression material 1000 can cover enough of the registration component 810 such that defining shapes, surfaces, edges, and/or corners can be molded into the impression material 1000. Similarly, the impression material 1000 can cover enough of the bone 114 such that one or more defining features of the bone 114 can be molded into the impression material 1000.

Figure 10B:
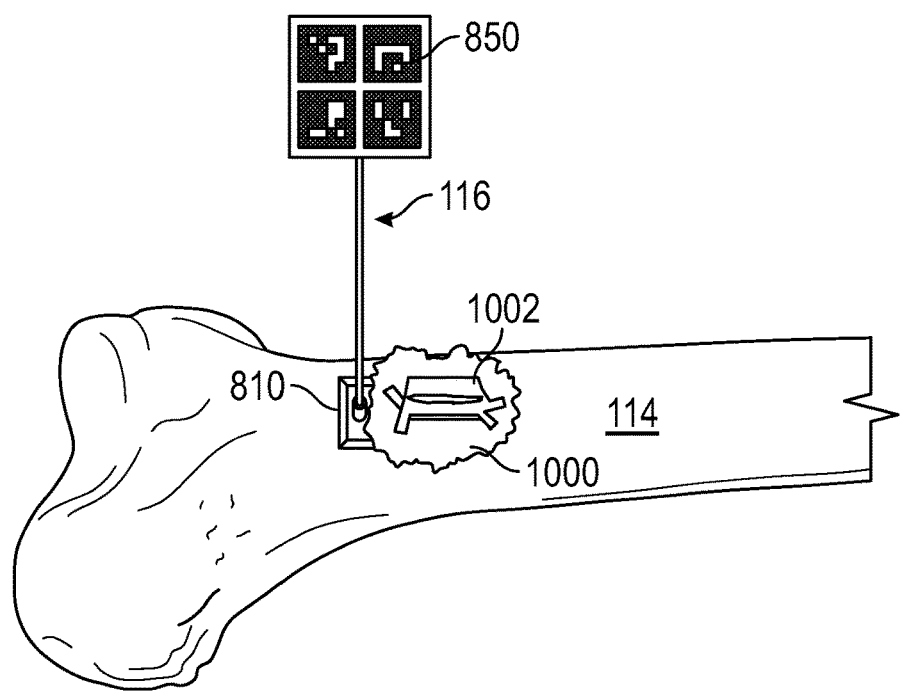

In at least one example, as illustrated in FIG. 10B, an enforcement component 1002 can be placed on and/or in the impression material 1000. The enforcement component 1002 can provide support to the impression material 1000 so that the impression material 1000 is able to better retain its shape after removal. For example, the enforcement component 1002 can function similar to rebar supporting concrete in construction. In at least one example, the enforcement component 1002 can include or be formed as a handle to ease removal of the impression material 1000 from the marker 116 and the bone 114. When the impression material 1000 either hardens or captures an adequate impression of at least a portion of the registration component 810 and the bone 114, the impression material 1000 can be removed.

Figure 10C:
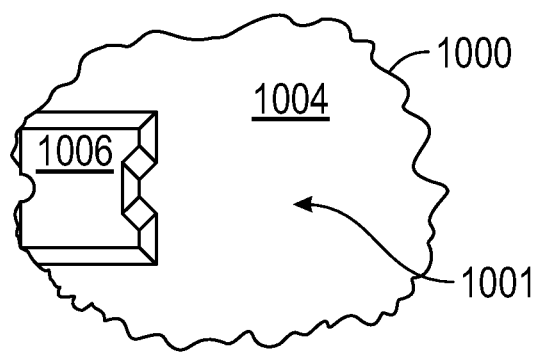
Figure 10D:
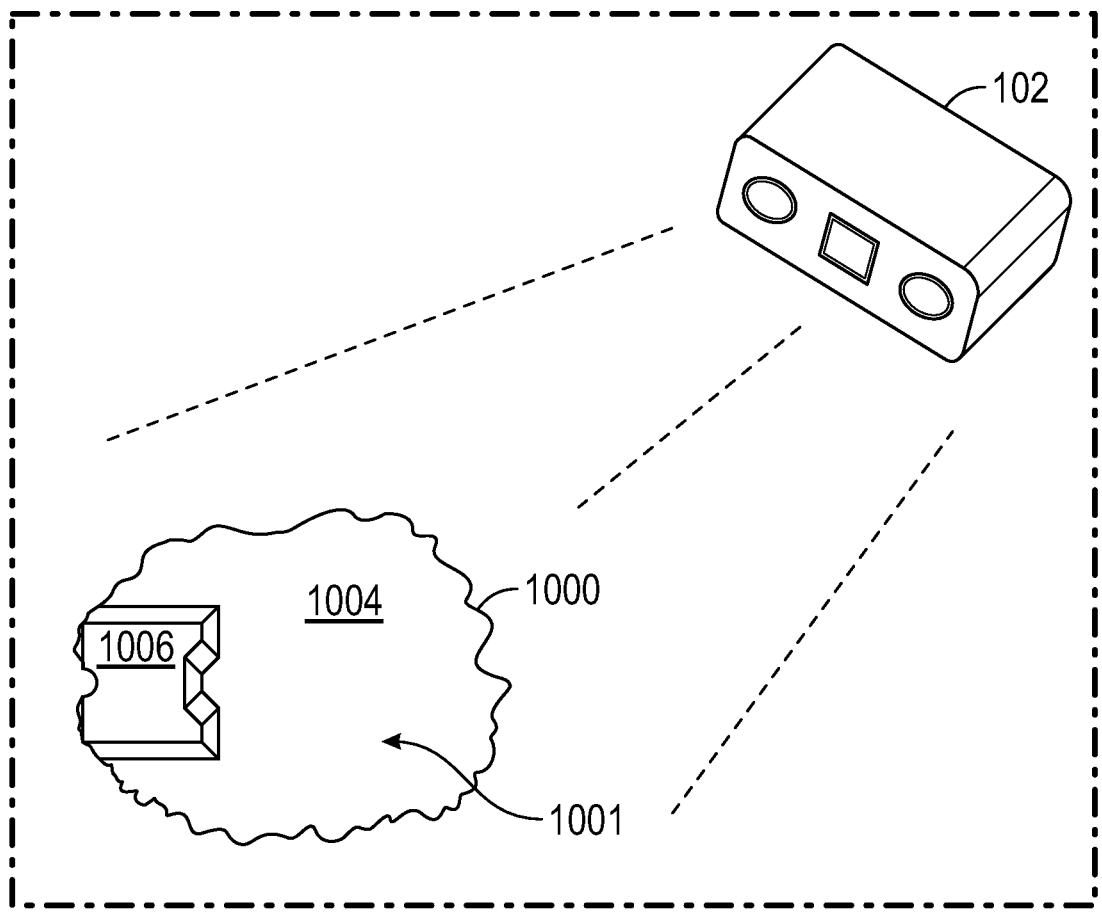

FIG. 10C illustrates the underside 1001 of the impression material 1000, showing the bone negative impression 1004 and the marker negative impression 1006. The underside 1001 of the impression material 1000 including the bone negative impression 1004 and the marker negative impression 1006 is then scanned by the 3D surface scanner 102. The controller 108 can reverse the normal vectors of the bone negative impression 1004 and the marker negative impression 1006 such that the controller 108 has a scan of the bone 114 and the marker 116. By using the impression material 1000, the 3D surface scanner 102 does not have to be in direct sight of the bone 114 and marker 116. Accordingly, when the bone 114 and the marker 116 are not easily accessible by the 3D surface scanner 102, the impression material 1000 can be utilized to provide a scan of the bone 114 and the marker 116 for registration.

Figure 11A:
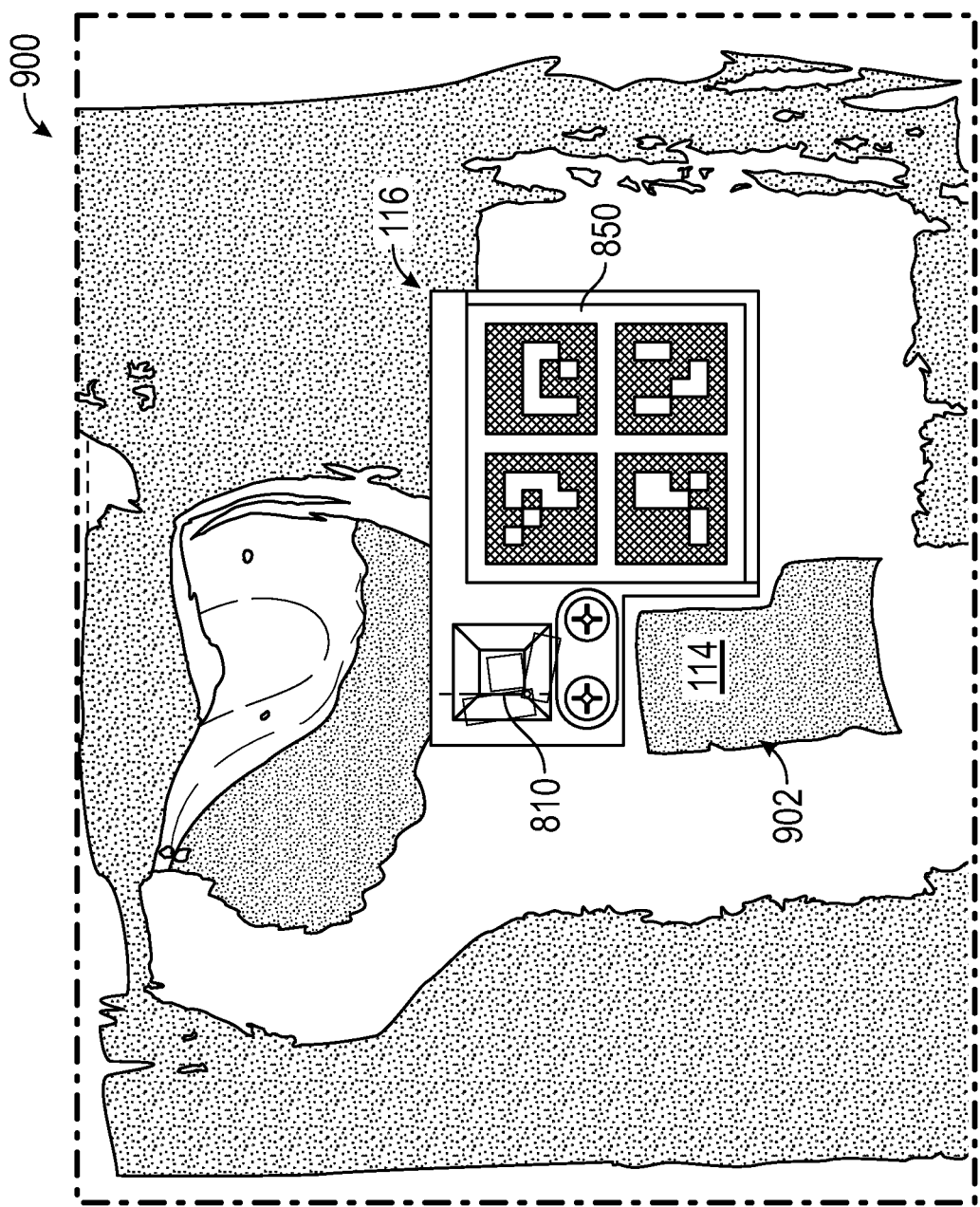
FIG. 11A is a diagram illustrating a bone image scanned by the 3D surface scanner.

For example, as illustrated in FIG. 11A, the controller 108 can create a digital recreation 900 of at least a portion of the bone 114 and at least a portion of the marker 116 based on the scan of the marker 116 and bone 114. For example, the digital recreation 900 can include a 3D point cloud. For example, each digital recreation 900 can capture at least an area of 100 millimeters by 100 millimeters with about 1 million points such that the 3D point cloud created from the 3D surface scanner 102 can have an exemplary resolution of about 20 points/mm$^2$. The preoperative image 110 can have a resolution of about 2 points/mm$^2$. In at least one example, to reduce the computational cost, the point cloud of the digital recreation 900 can be down-sampled to the same resolution as the preoperative image 110. In at least one example, the digital recreation 900 can include a 3D mesh. The 3D mesh can include, for example a 3D point cloud where each point is connected.

In some examples, in the digital recreation 900, many points may originate from the surrounding and/or background areas which are also captured and constructed by the 3D surface scanner 102, and are not relevant in the next alignment procedure. The images of the surrounding and/or background areas may be removed using computer software, for example with the controller 108, leaving only the exposed bone 114 and/or at least a portion of the marker 116 such as at least a portion of the registration component 810. In some examples, the images of the surrounding and/or background areas may be removed by an assistant and/or the doctor. In some examples, the images of the surrounding and/or background areas may be removed automatically without human assistance by the controller 108.

Figure 11B:
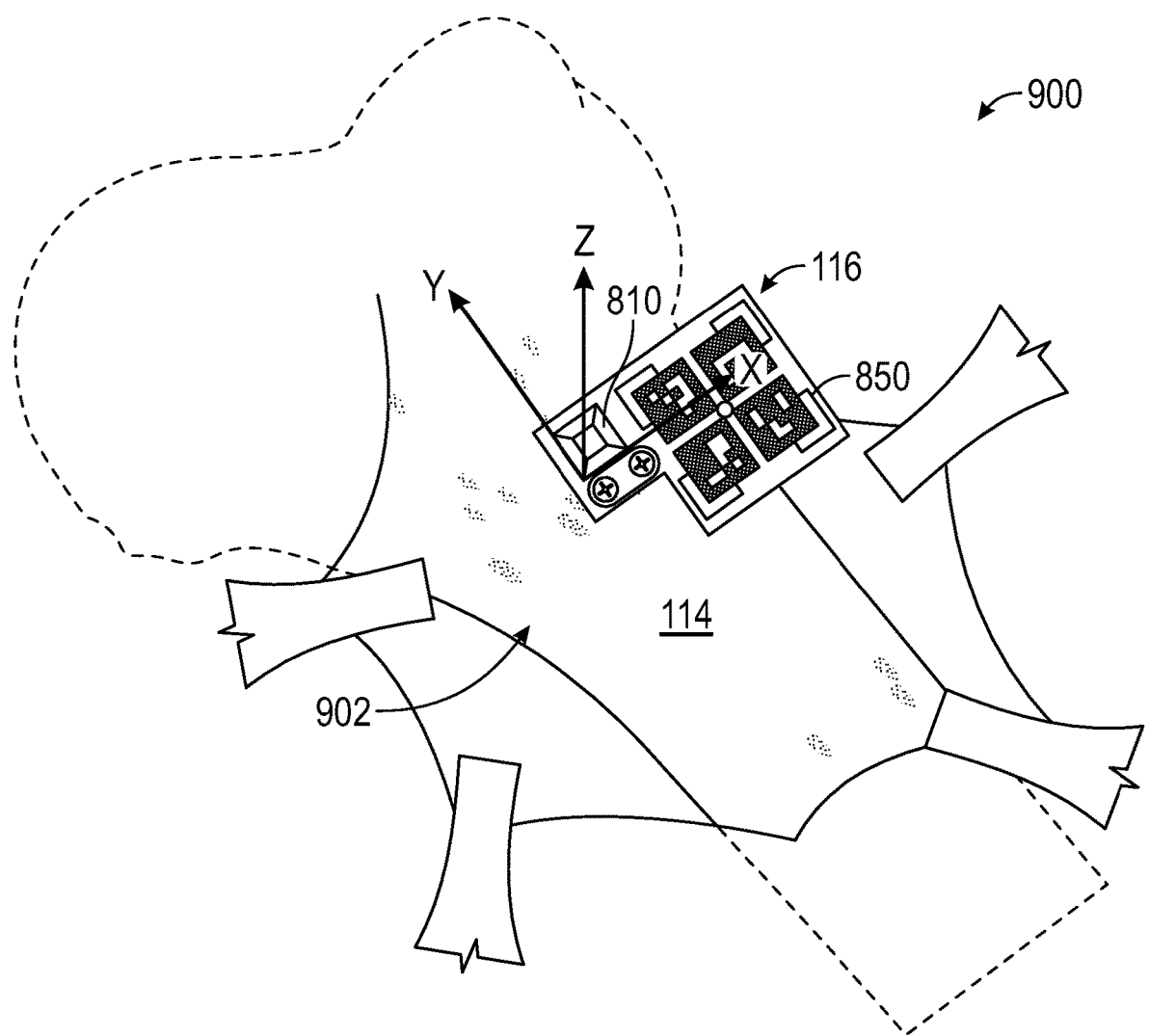
FIGS. 11B-11D are diagrams illustrating analysis and registration of the bone image with the preoperative image.
Figure 11C:
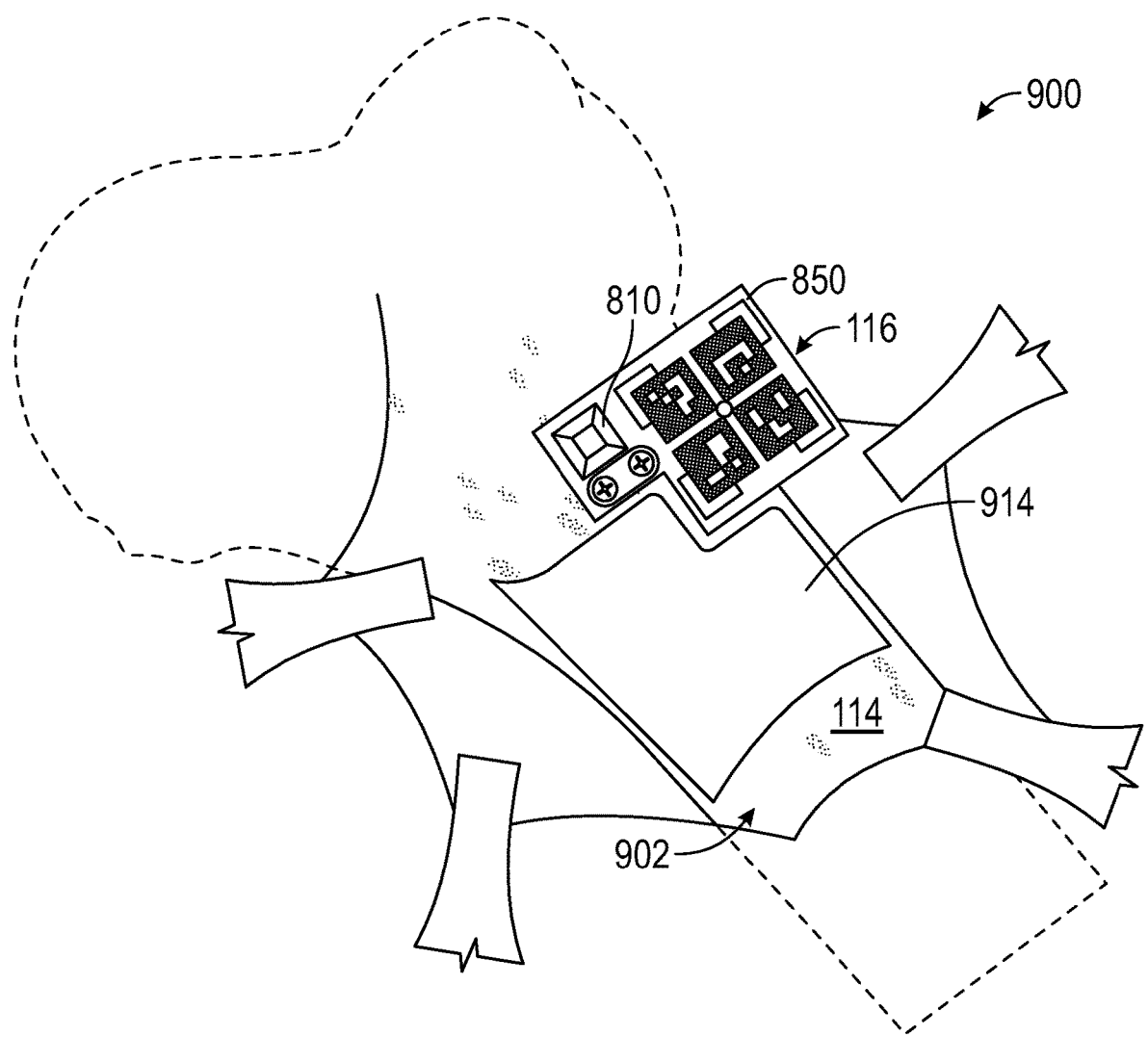

As illustrated in FIG. 11B, the orientation of the marker 116 and subsequently the bone 114 can be determined using the controller 108. For example, the flat surfaces of the registration component 810 can be selected and one or more intersected edges and/or corners of the registration component can be extracted. As the shape and/or size of the registration component 810 is stored in the controller 108, the controller 108 can then determine the orientation of the registration component 810 along the X-axis, the Y-axis, and/or the Z-axis. As illustrated in FIG. 11C, the exposed bone area 914 without tissue is selected to create a bone scan 902. The marker 116 and the bone 114 are then registered, and the relationship between the bone 114 and the marker 116 is determined.

Figure 11D:
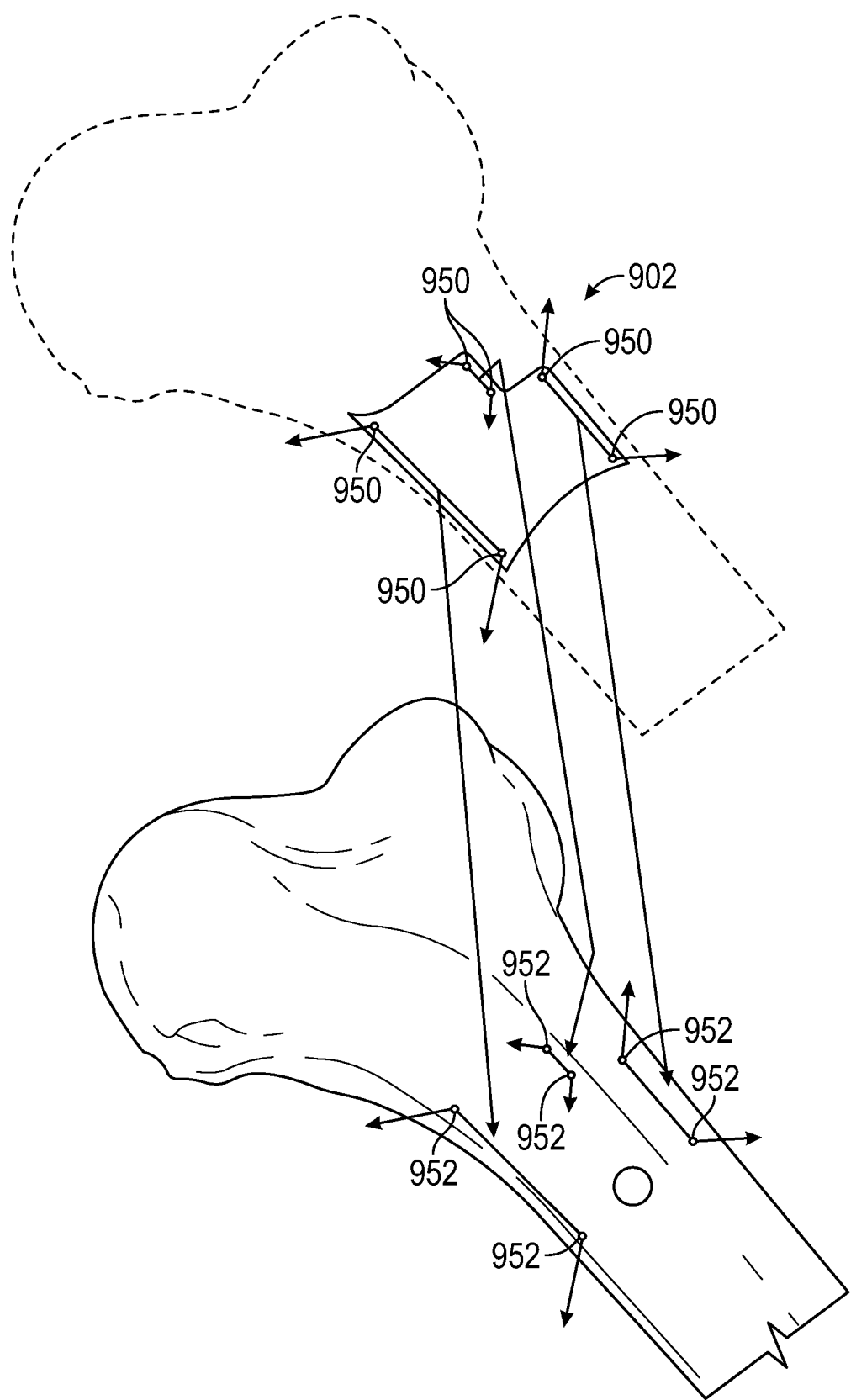

After the digital recreation 900 of the bone 114 is obtained and processed, as illustrated in FIG. 11D, the bone scan 902 is aligned with the preoperative bone image 115 such that the preoperative plan can be correlated with the physical bone and surgical process in real time.

In at least one example, a surface matching algorithm can be utilized by the controller 108 to align the bone scan 902 with the bone image 115. The surface matching algorithm can produce a number of highest possible rigid body homogenous transformations that can potentially align the two 3D models—the bone scan 902 and the bone image 115. The algorithm can build up a descriptor, called the point pair feature (PPF), for every two points 950 on the scanned surface of the bone scan 902. The algorithm can then find the two corresponding points 952 in the CT-scan model of the bone image 115 with similar or the same features as the bone scan 902. For the two corresponding pairs of points 950, 952 matched, the algorithm gives one vote for the homogenous transformation between the two corresponding pairs of points 950, 952. After finishing a predetermined number of matched PPF to satisfy the algorithm, a number of homogenous transformations with the highest votes are likely to become the best estimated homogenous transformations. The outcome of a successful execution of the surface matching algorithm, is a predetermined number of homogenous transformations with the highest votes.

An iterative closest point (ICP) algorithm can be applied to find the best match among the homogenous transformations obtained in the previous step by the surface matching algorithm. With each homogenous transformation, the bone scan 902 and the bone image 115 are brought closer. For example, the bone scan 902 and the bone image 115 can be brought together. Using the ICP algorithm, the corresponding points 950, 952 on the bone scan 902 and the bone image 115 are identified by a nearest point search. The ICP algorithm then computes the sum of the errors and/or discrepancies between all such corresponding points 950, 952 on the bone scan 902 and the bone image 115 associated with each of the homogenous transformations from the previous step. Such errors may be minimized to find the best alignment and the resulting homogenous transformation.

Finally, after the ICP algorithm is completed for all homogenous transformations between the bone scan 902 and the bone image 115, the homogenous transformation with the smallest error between the bone scan 902 and the bone image 115 is selected as final result. This homogenous transformation is used for the subsequent alignment of the bone scan 902 and the bone image 115 and/or future procedures.

Figure 12A:
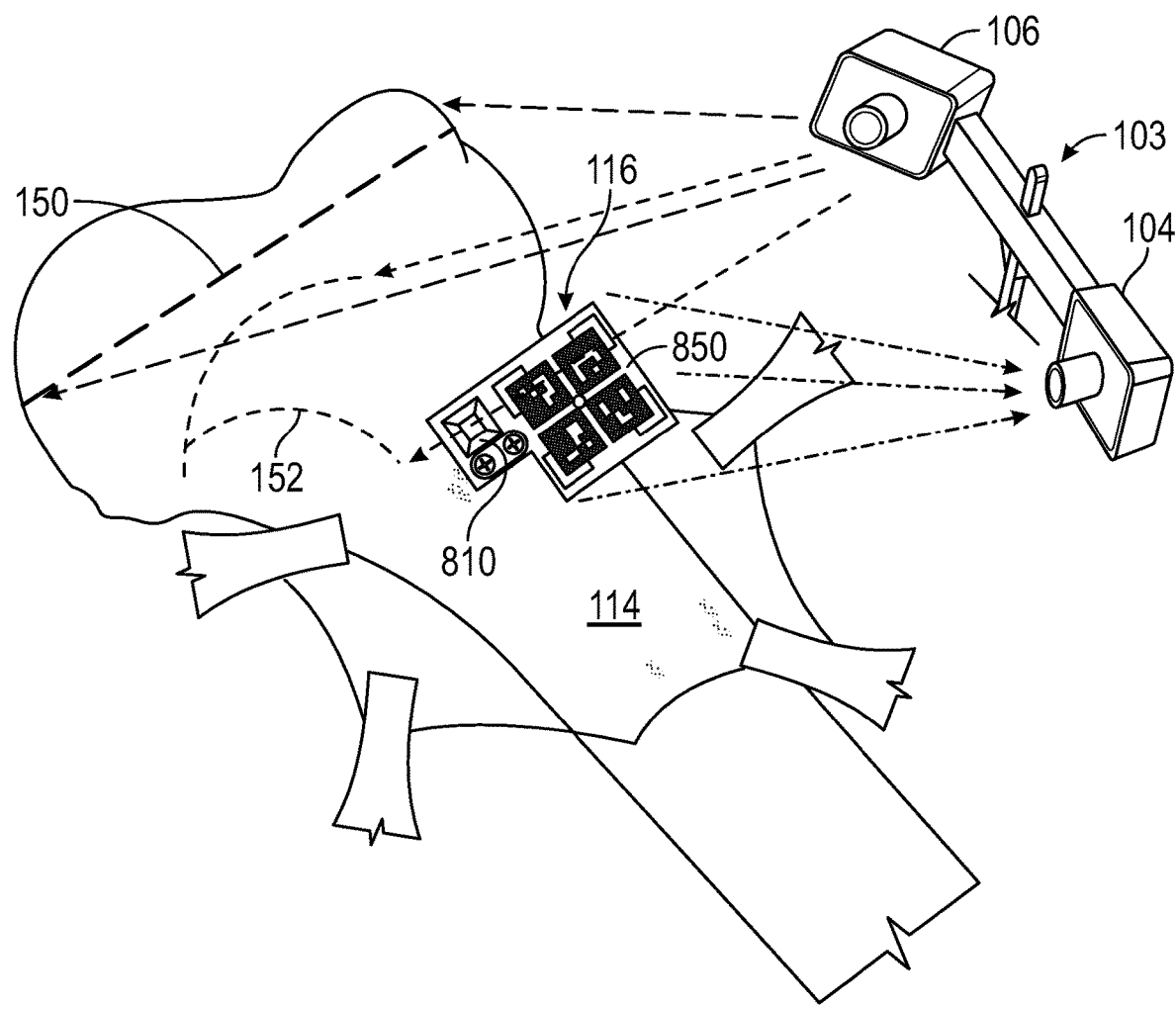
FIGS. 12A and 12B are diagrams illustrating a camera tracking in real time a tracking component of a marker and a projector projecting cutting lines and alignment lines.

Once the bone scan 902 is aligned with the bone image 115, the marker 116 is registered in the controller 108. Accordingly, the controller 108 is able to track, as illustrated in FIG. 12A using the camera 104 to follow the movement of the tracking component 850, the orientation and/or movement of the bone 114 during surgery. As the relationship such as the distance and orientation between the bone 114, the registration component 810, and the tracking component 850 is registered in the controller 108, as the tracking component 850 moves in the images captured by the camera 104, the controller 108 is able to accurately calculate the location and/or orientation of the bone 114.

In some examples, other suitable registration systems and methods may be utilized to register a preoperative bone image 115 with one or more bone scans 902 so that the movement and/or orientation of the bone 114 can be tracked during surgery.

For example, the bone 114 can be touched with a probe that has known dimensions and one or more reflective markers. This method can rely on a motion tracking device which includes at least two infrared (or near-infrared) cameras. The relative pose of each camera is fixed and pre-defined (or pre-calibrated). Two probes may be needed to be tracked by the motion tracking device intraoperatively. First, the surgeon affixes a reference probe to the target bone. After that, the surgeon uses a hand probe to touch the surface of the target bone 114, for example a few dozen times. Each touch can correspond to one 3D point with respect to the reference probe. After touching the bone 114 with the probe, a 3D point cloud is built with reference to the reference probe and can be used for registration to the pre-operative image 115.

In other examples, registration of the bone 114 can be performed by an imaging device. For example, a motion tracking device can be utilized. The imaging device can include intraoperative computed tomography (CT). Markers can be fixed on the bone 114 to be tracked by CT. One or more reference array probes can be fixed on the target bone 114 to be trackable by CT. A CT scan can then be conducted, and a 3D image can be built with respect to the reference probe. This intraoperative image can be used to register with the preoperative image 115. In some examples, the imaging device can instead include cone beam CT. In some examples, the imaging device can include magnetic resonance imaging (MRI). In some examples, the imaging device can include x-rays such as fluoroscopic x-rays, for example from multiple planes. The acquired 2D images, together with the obtained x-ray probe position and/or orientation on each image, can be used to generate an X-ray volume composed of regular spaced data and to form a 3D image. The 3D image can then be used for registration.

In other examples, a 3D ultrasound may be utilized. The images may be acquired with a probe having a passive position sensor. The sensor can use spherical, retroreflective markers that reflect infrared light emitted by illuminators on the tracker. The tracker can measure the probe spatial position and/or orientation. The acquired images, along with the spatial position and/or orientation on each image, can be used to generate an ultrasound volume composed of regular spaced data and to form a 3D image. A 3D point cloud and/or mesh can be generated with the ultrasound data and registered to the preoperative image 115.

Figure 12B:
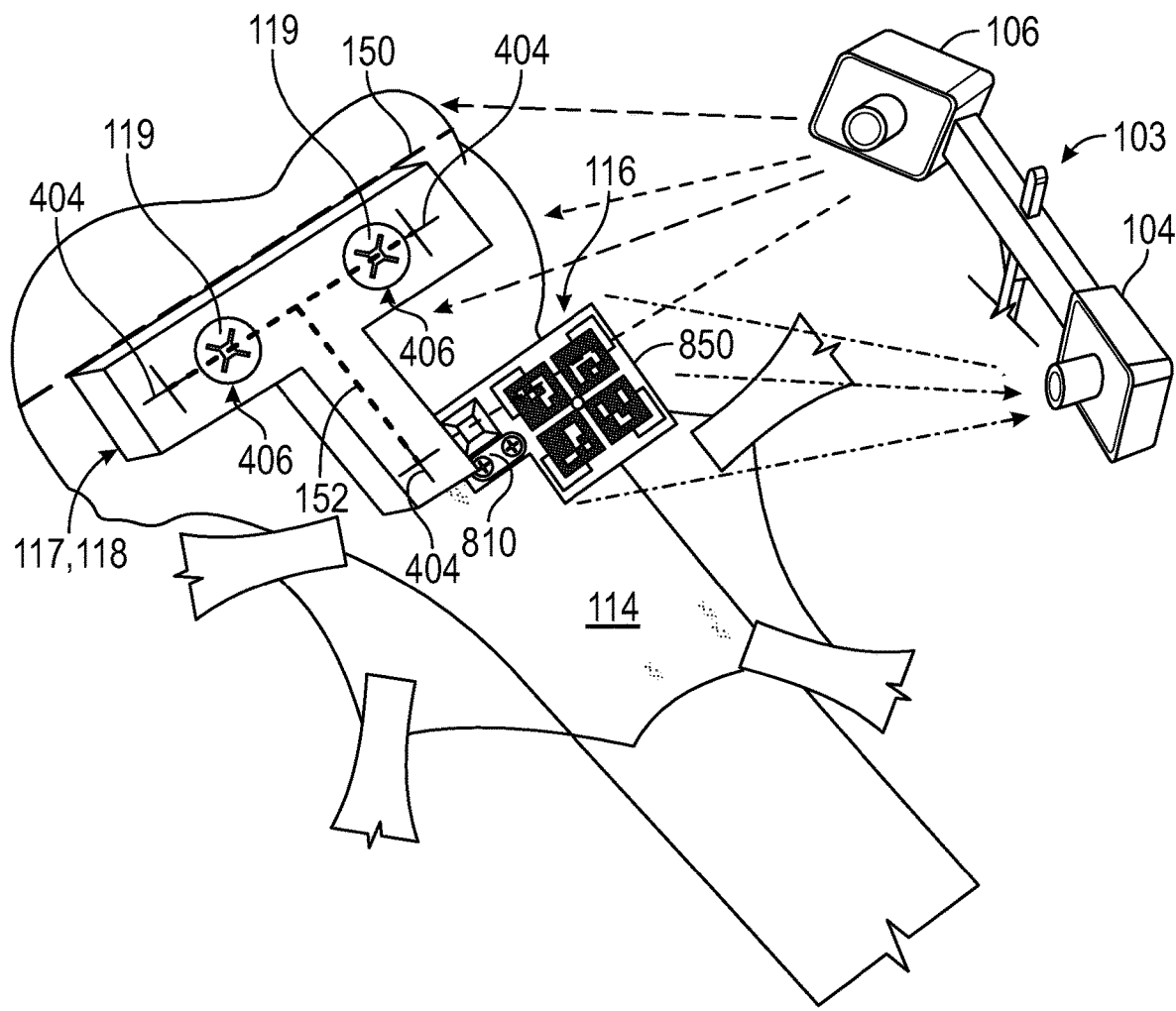

In at least one example, as illustrated in FIG. 12A, the projector 106 is operable to project a cutting line 150 and/or an alignment line 152 onto the bone 114. The cutting line 150 and/or the alignment line 152 can be projected as lines of shapes of light. The color of the cutting line 150 and/or the alignment line 152 can vary as desired. In some examples, the color of the cutting line 150 and the color of the alignment line 152 can be different to differentiate the lines. For example, the color of the cutting line 150 can be red, and the color of the alignment line 152 can be green. In some examples, the color of the cutting line 150 and the color of the alignment line 152 can be the same. The cutting line 150 is operable to indicate the path and/or plane that the surgical blade should cut the bone 114. As shown in FIGS. 12A and 12B, the cutting line 150 is shown as a straight line. In some examples, at different viewing angles, the projected cutting line 150 can appear curved, representing the intersection line between the cutting plane 410 and the bone surface 114.

The alignment line 152 indicates the alignment of a jig 117 to ensure the jig 117 provides an accurate guide for the surgical blade to cut the bone 114 along the cutting line 150. For example, FIG. 12B illustrates a jig 117 being coupled with the bone 114 using fasteners 119. The fasteners 119 can include screws, pins, or any other suitable surgical fastener to couple the jig 117 with the bone 114. As illustrated in FIG. 12B, the jig 117 is a linear jig 118, and the cutting line 150 is aligned with the front surface 402 of the jig 117. As discussed above, different jigs 117 can be utilized to accommodate different cutting lines 150 with different shapes, paths, and/or planes. The alignment line 152 is aligned with the alignment markers 404 of the jig 117. Accordingly, the jig 117 is in the correct and accurate placement and/or alignment on the bone 114 to guide the correct and accurate cut of the bone 114 by the surgical blade along the cutting line 150. As shown in FIG. 12A, the alignment line 152 being projected on the bone 114 is not a straight line and has curves and waves differing from the lines desired to match the alignment markers 404 on the jig 118 as illustrated in FIG. 12B. The alignment line 152 has this appearance before the jig 117 is positioned because the alignment line 152 is being projected on the bone 114 instead of the jig 117. The bone 114 may have curves and angles that are different from the jig 117. Additionally, in some examples, the surface of the jig 117 with the alignment markers 404 may be at a different depth or distance from the projector 106 than the surface of the bone 114. Accordingly, the alignment line 152 may have a different appearance on the bone 114 than on the jig 117 when the jig 117 is in position.

As the marker 116 is registered with the controller 108, the light projected on the bone 114 by the projector 106, such as the alignment line 152 and/or the cutting line 150, can be adjusted as the bone 114 is moved during surgery. The camera 104 captures images and/or videos in real-time, and the controller 108 can track the movement of the bone 114 in real-time by determining the movement and/or orientation of the tracking component 850 of the marker 116. As the bone 114 and correspondingly the marker 116 moves, the controller 108 can adjust the light projected on the bone 114 by the projector 106 in real-time to ensure the positioning of the light is as desired. For example, the bone 114 and the marker 116 may move, and the controller 108 can control the projector 106 in real-time to adjust the light such that the light, such as the cutting line 150 and/or the alignment line 152, corresponds with the preoperative plan.

Once the alignment of the jig 117 is confirmed such that the cutting line 150 is aligned with the front surface of the jig 117 and/or the alignment lines 152 are aligned with the alignment markers 404 on the jig 117, the surgeon can proceed with cutting the bone 114. The surgical blade is guided by the front surface of the jig 117 to ensure an accurate and precise cut of the bone 114.

In at least one example, the jig 117 may be correctly aligned when initially positioned and prior to being fastened to the bone 114 or an intermediate component. However, when the jig 117 is fastened in place, the jig 117 may become misaligned. In such a scenario, the positioning of the jig 117 may need to be fine-tuned and adjusted to bring the jig 117 back into the correct alignment and positioning. The positioning adjustment of the jig 117 may be along the X-axis, Y-axis, Z-axis, and/or tilt along any combination of the X, Y, and/or Z axes. FIGS. 13A-13G illustrate an exemplary position mechanism 1300 which is operable to adjust, if desired or needed, the positioning of the jig 117 after the jig 117 has been secured.

Figure 13A:
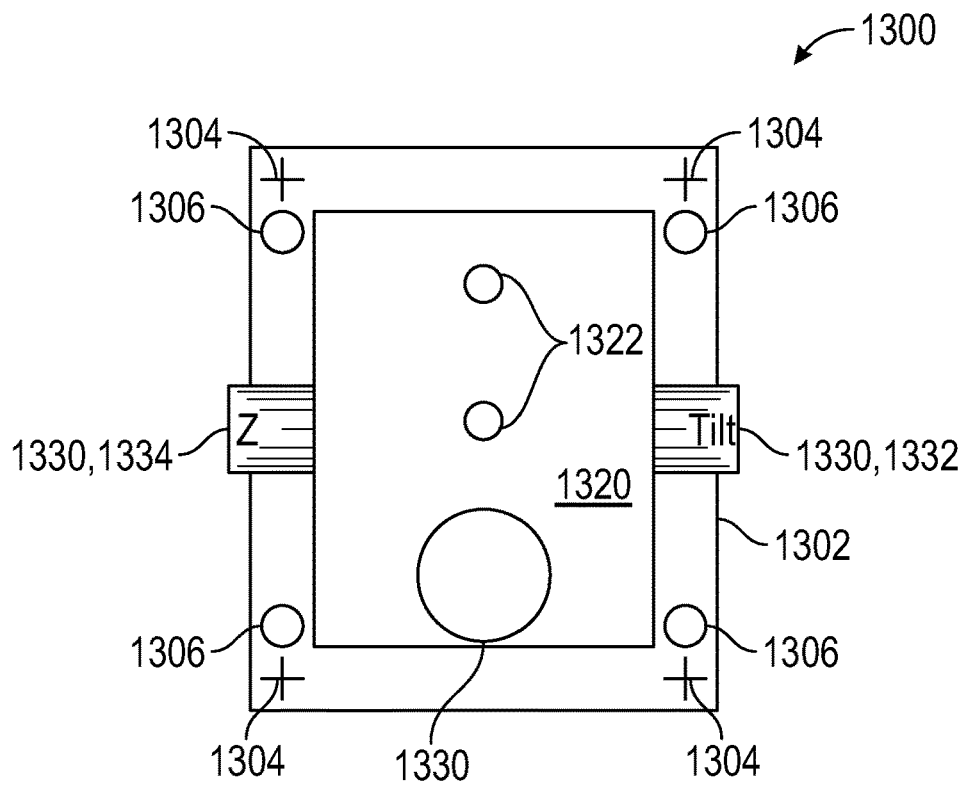
FIGS. 13A-13G are diagrams illustrating an exemplary position mechanism operable to adjust the positioning and alignment of a jig.
Figure 13B:
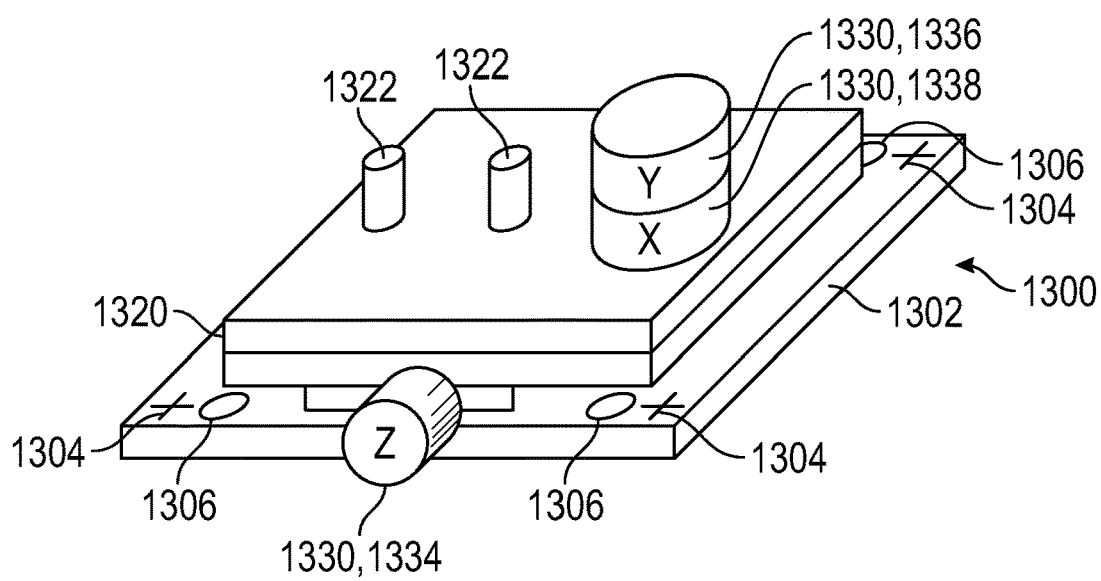
Figure 13C:
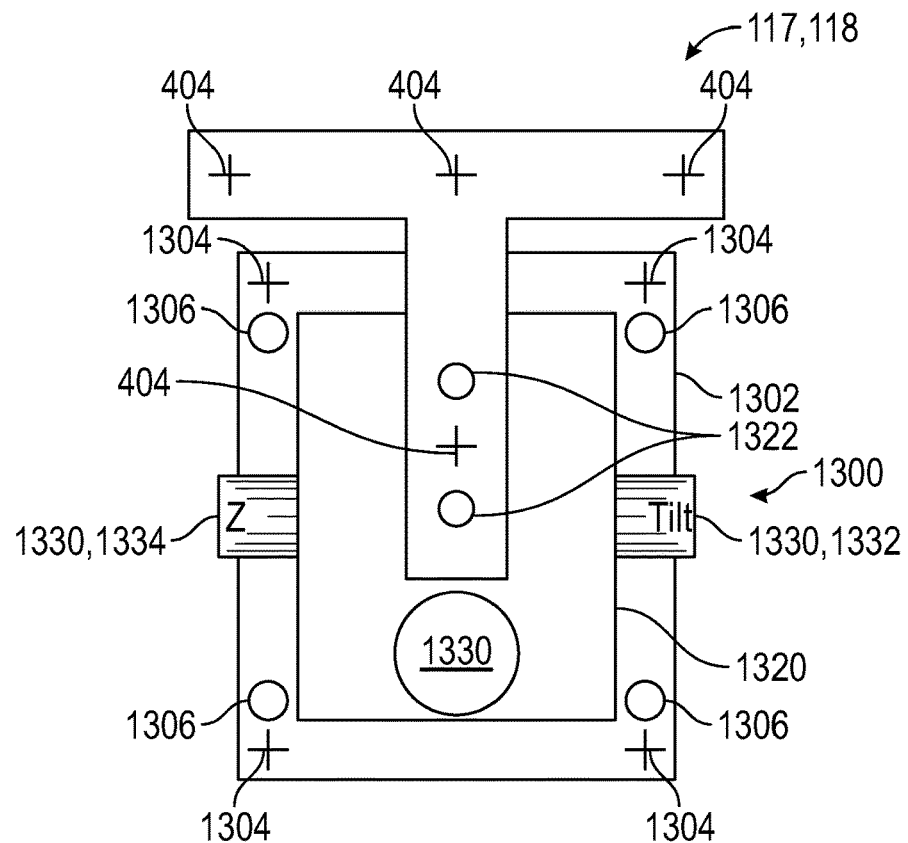
Figure 13D:
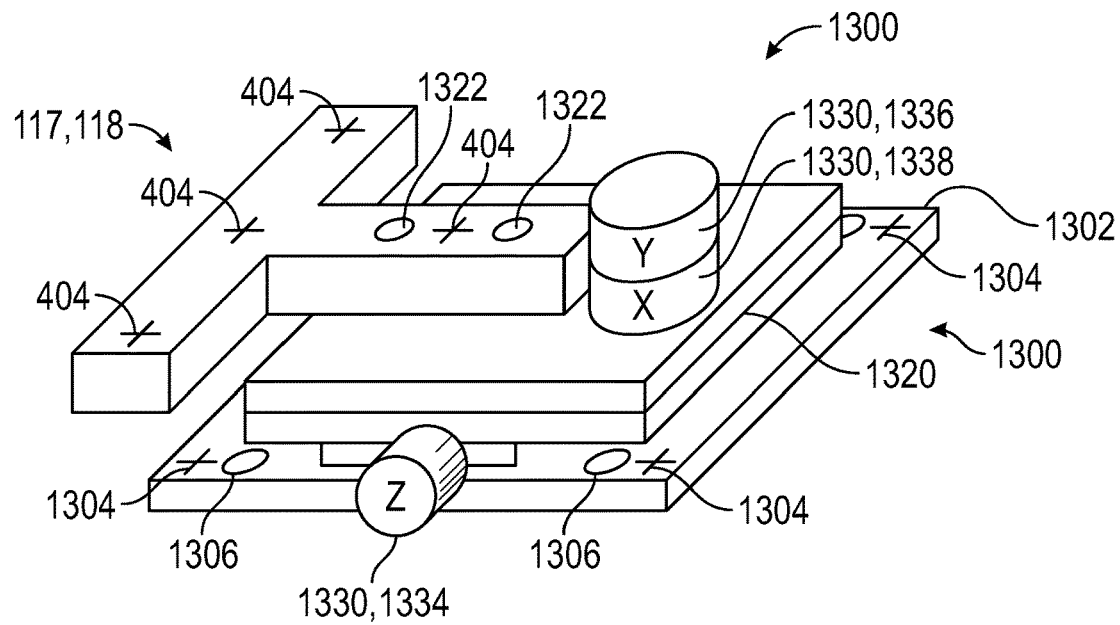

FIGS. 13A and 13B illustrate the position mechanism 1300. The position mechanism 1300 can include a base 1302 operable to be fixed to the bone 114. While the disclosure discusses fixing the position mechanism 1300 to the bone 114, in some examples, the position mechanism 1300 can be positioned and fixed proximate to the bone 114 so long as the jig 117 can be correctly positioned. For example, the base 1302 can include fixation components 1306 which are operable to fix the position mechanism 1300 with the bone 114. The fixation components 1306 can include recesses and/or apertures through which fixation elements 1350 (shown in FIGS. 13F and 13G) can couple the position mechanism 1300 to the bone 114. For example, the fixation elements 1350 can include screws, pins, or any other suitable mechanism operable to couple the position mechanism 1300 to the bone 114.

In some examples, as illustrated in FIGS. 13A and 13B, the position mechanism 1300 can include a plurality of position markers 1304 operable to ensure the correct and precise alignment of the position mechanism 1300. When a position projection 154 (as illustrated for example in FIG. 13E) is aligned with the position markers 1304, the position mechanism 1300 is accurately and precisely positioned. The positioning and placement of the position mechanism 1300 can, for example, be determined during preoperative planning by the controller 108. In some examples, the position mechanism 1300 may not include position markers 1304. As illustrated in FIGS. 13A-13G, four position markers 1304 are located in each of the four corners of the base 1302. In some examples, the location of the position markers 1304 can vary as desired so long as the position markers 1304 can align with the position projection 154 to ensure the accurate and precise positioning of the position mechanism 1300.

In at least one example, the position mechanism 1300 can include a platform 1320 which is operable to move relative to the base 1302 and/or the bone 114. The platform 1320 is operable to receive and/or be coupled with the jig 117. The platform 1320 can include couplers 1322 operable to be coupled with the jig 117 to secure the jig 117. For example, as illustrated in FIGS. 13A-13D, the couplers 1322 can include at least one prong operable to be inserted into and/or through the jig 117 to secure the jig 117 to the platform 1320. As illustrated in FIGS. 13A-13D, the couplers 1322 can include two prongs disposed linearly from one another to align the jig 117 and prevent undesired movement of the jig 117.

The platform 1320 can move relative to the base 1302 and/or the bone 114 along the X-axis, Y-axis, Z-axis, and/or tilt along any combination of the X, Y, and/or Z axes. In at least one example, as illustrated in FIGS. 13A-13D, the position mechanism 1300 can include position controls 1330 which are operable to be adjusted to move the platform 1320. For example, the position controls 1330 can include knobs which are operable to be manually adjusted, such as twisted or moved. As illustrated in FIGS. 13A-13D, the position controls 1330 can include an X-axis control 1338 operable to move the platform 1320 along the x-axis, a Y-axis control 1336 operable to move the platform 1320 along the y-axis, a Z-axis control 1334 operable to move the platform 1320 along the z-axis, and/or a tilt control 1332 operable to tilt the platform 1320 along any of the x-, y-, and/or z-axes. In some examples, the position controls 1330 can be powered by one or more motors. In some examples, the position controls 1330 can be controlled remotely by a separate device such as a joystick, a remote controller, mouse, and/or keyboard coupled to the controller 108. In some examples, the controller 108 may automatically adjust the position controls 1330 without human assistance until the jig 117 is correctly aligned and positioned.

Figure 13E:
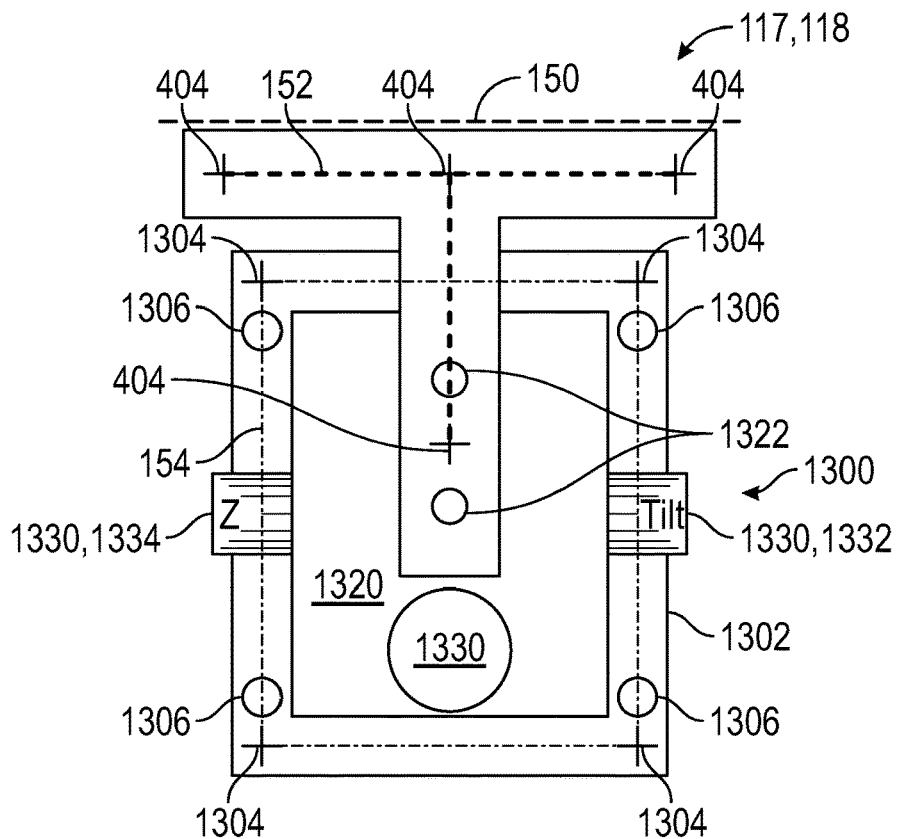

FIG. 13E illustrates a jig 117 which is coupled with a position mechanism 1300. As shown in FIG. 13E, the base 1302 of the position mechanism 1300 is not yet fixed to the bone 114. The jig 117 and the position mechanism 1300 are correctly positioned and aligned, as the cutting line 150 is aligned with the front surface of the jig 117, the alignment lines 152 are aligned with the alignment markers 404 on the jig 117, and, optionally, the position projection 154 is aligned with the position markers 1304.

Figure 13F:
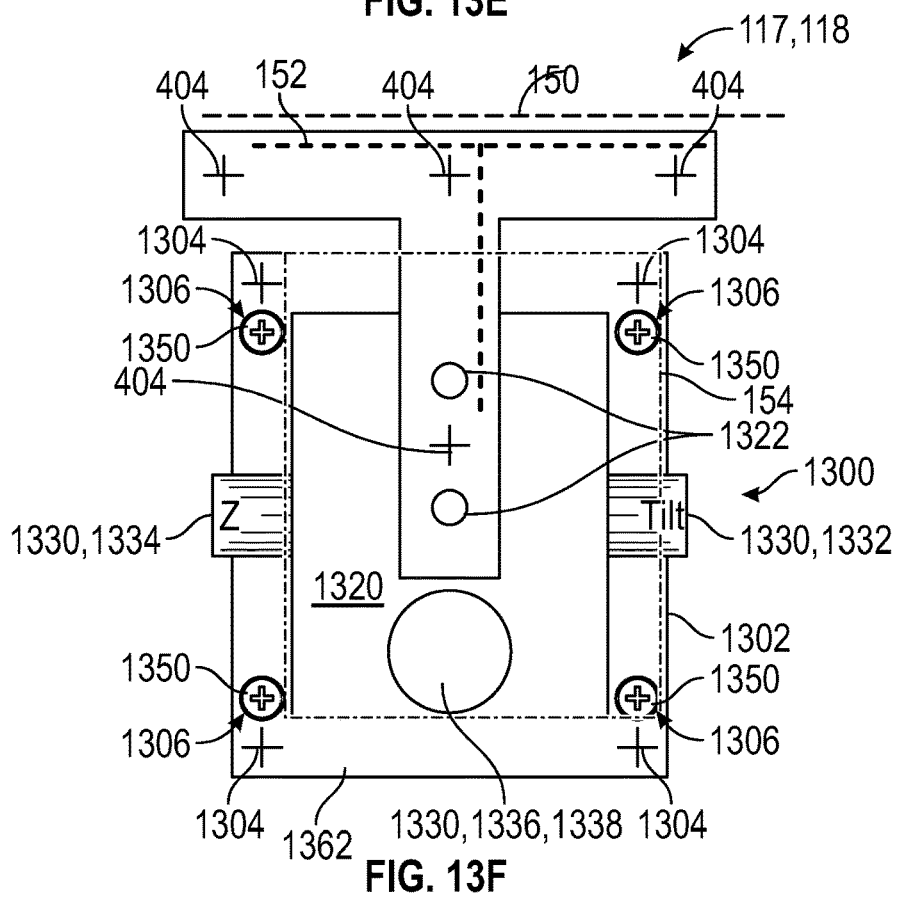
Figure 13G:
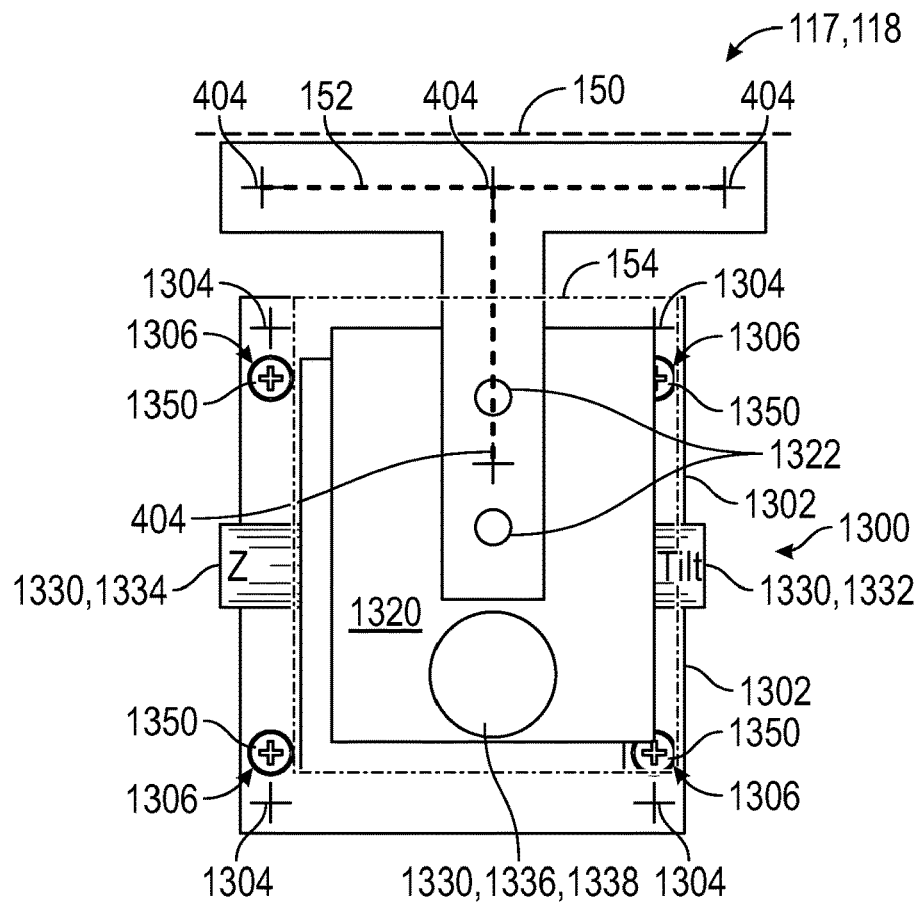

As illustrated in FIG. 13F, when the base 1302 of the position mechanism 1300 is fixed to the bone 114 by fixation elements 1350, the position mechanism 1300, and subsequently the jig 117, may become misaligned as shown in FIG. 13F. Accordingly, the cutting line 150 is not aligned with the front surface of the jig 117, the alignment lines 152 are not aligned with the alignment markers 404 on the jig 117, and, optionally, the position projection 154 is not aligned with the position markers 1304. As illustrated in FIG. 13F, the cutting line 150, the alignment lines 152, and the position projection 154 is offset to the upper right from the position mechanism 1300 and the jig 117. As the base 1302 of the position mechanism 1300 is fixed in place, the position mechanism 1300 cannot move. However, the positioning of the jig 117 needs to be fine-tuned and adjusted to adequately guide the surgical blade as the surgical blade cuts the bone 114. As illustrated in FIG. 13G, the platform 1320 is moved using the position controls 1330. The jig 117, being coupled with the platform 1320, moves along with the platform 1320. The jig 117 is then moved until the cutting line 150 aligns with the front surface of the jig 117 and/or the alignment lines 152 align with the alignment markers 404 on the jig 117. As can be seen in FIG. 13G, the base 1302 of the position mechanism 1300 did not move as the position line 154 is still not aligned with the position markers 1304.

In at least one example, the camera 104 continually monitors in real time the tracking component 850 of the marker 116 such that, even though the bone 114 may be moved around during surgery, the controller 108 controls the projector 106 to adjust the projected location(s) of the cutting line 150, the alignment lines 152, and/or the position projection 154. Accordingly, even if the bone 114 is moved, the jig 117 and/or the position mechanism 1300 can be positioned and aligned to accurately follow the preoperative plan.

Once the alignment of the jig 117 is confirmed such that the cutting line 150 is aligned with the front surface of the jig 117 and/or the alignment lines 152 are aligned with the alignment markers 404 on the jig 117, the surgeon can proceed with cutting the bone 114. The surgical blade is guided by the front surface of the jig 117 to ensure an accurate and precise cut of the bone 114.

Figure 14:
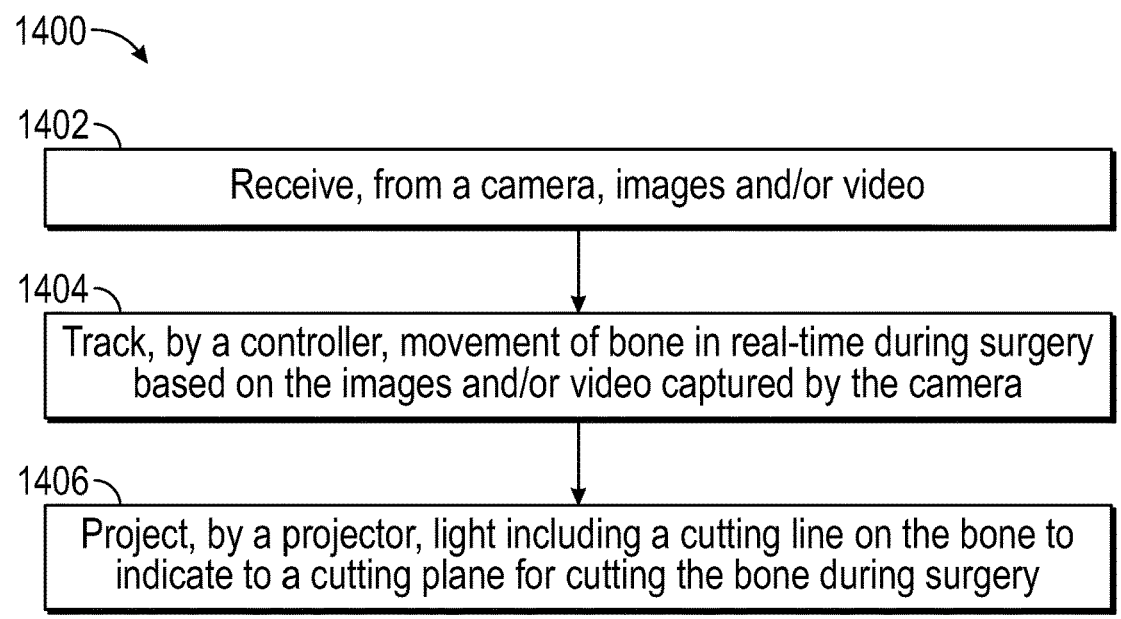
FIG. 14 is a flow chart illustrating an example of a bone surgery that may be used in accordance with the present disclosure.

Referring to FIG. 14, a flowchart is presented in accordance with an example embodiment. The method 1400 is provided by way of example, as there are a variety of ways to carry out the method. The method 1400 described below can be carried out using the configurations illustrated in FIGS. 1-13G, for example, and various elements of these figures are referenced in explaining example method 1400. Each block shown in FIG. 14 represents one or more processes, methods or subroutines, carried out in the example method 1400. Furthermore, the illustrated order of blocks is illustrative only and the order of the blocks can change according to the present disclosure. Additional blocks may be added or fewer blocks may be utilized, without departing from this disclosure. The example method 1400 can begin at block 1402.

At block 1402, images and/or video are received from a camera. The camera can capture the images and/or video in real-time during surgery and transmit the images and/or video to a controller.

At block 1404, the controller can track the movement of bone in real-time during surgery based on the images and/or video captured by the camera. In at least one example, the controller can track the movement of a tracking component of a marker coupled with the bone in the images and/or video captured by the camera. In some examples, the tracking component can include a two-dimensional pattern and/or one or more reflecting tracking features operable to be scanned by the camera and recognized by the controller to track the movement of the tracking component. The two-dimensional pattern can include a barcode and/or a QR code.

In at least one example, a registration component of the marker coupled with the bone can be registered into the controller such that the location and/or orientation of the marker in relation to the bone is determined. The location and/or orientation of the marker in relation to the bone can be registered into the controller, for example, by scanning at least a portion of a three-dimensional body of the registration component and at least a portion of the bone. The registration component can have a predetermined position relative to the tracking component. Accordingly, when the registration component is registered in relation to the bone, the location and/or orientation of the tracking component in relation to the bone is also then known.

At block 1406, a projector can project light including a cutting line on the bone to indicate a cutting plane for cutting the bone during surgery. The cutting plane can be input into the controller during preoperative planning prior to surgery. The cutting line can form one or more shapes including one or more of the following: one or more dots, one or more lines, one or more circles, one or more triangles, and/or one or more irregular shapes. In some examples, the projector can have a predetermined position relative to the camera. Accordingly, the controller can determine the relationship between the angles and/or distance of the bone captured in the images and/or video and accurately determine the light such as the cutting line to be projected onto the bone.

In at least one example, a jig can be coupled with the bone. The jig can be operable to guide a surgical blade during the cutting of the bone during surgery. In some examples, the jig can include a plurality of alignment markers. The controller can be further operable to control the projector to project the light to include one or more alignment lines to correspond with the alignment markers such that the alignment lines indicate a predetermined position of the jig based on preoperative planning.

In some examples, the light projected on the bone can be adjusted in real time when the bone is moved. As the marker is registered, the controller can track the movement of the tracking component of the marker to determine the movement of the bone in real-time. The light projected can then be adjusted in real-time to ensure the light such as the cutting line and/or the alignment lines are consistently accurately and precisely positioned. The surgeon can then conduct surgery with assurance that the cutting of the bone is exactly as desired based on the preoperative plan.

Numerous examples are provided herein to enhance understanding of the present disclosure. A specific set of statements are provided as follows.

Statement 1: A surgical system is disclosed comprising: a camera operable to capture images and/or video; a projector operable to project light; and a controller communicatively coupled with the camera and the projector, the controller operable to: track movement of bone in real-time during surgery based on the images and/or video captured by the camera; and control the projector to project the light including a cutting line on the bone to indicate a cutting plane for cutting the bone during surgery.

Statement 2: A surgical system is disclosed according to Statement 1, wherein the projector has a predetermined position relative to the camera.

Statement 3: A surgical system is disclosed according to Statements 1 or 2, further comprising a marker coupled with the bone, the marker including a tracking component, wherein the controller tracks the movement of the bone by tracking the movement of the tracking component in the images and/or video captured by the camera.

Statement 4: A surgical system is disclosed according to Statement 3, wherein the tracking component includes a two-dimensional pattern and/or one or more reflecting tracking features operable to be scanned by the camera and recognized by the controller to track the movement of the tracking component.

Statement 5: A surgical system is disclosed according to Statement 4, wherein the two-dimensional pattern includes a barcode and/or a QR code.

Statement 6: A surgical system is disclosed according to any of preceding Statements 3-5, wherein the marker includes a registration component, wherein the registration component is operable to be registered with the controller such that the location and/or orientation of the marker in relation to the bone is determined.

Statement 7: A surgical system is disclosed according to Statement 6, wherein the registration component has a predetermined position relative to the tracking component.

Statement 8: A surgical system is disclosed according to Statements 6 or 7, wherein the registration component includes a three-dimensional body, wherein at least a portion of the three-dimensional body and at least a portion of the bone is scanned into the controller to register the location and/or orientation of the marker in relation to the bone.

Statement 9: A surgical system is disclosed according to any of preceding Statements 1-8, wherein the cutting plane is input into the controller during preoperative planning prior to surgery.

Statement 10: A surgical system is disclosed according to any of preceding Statements 1-9, wherein the light projected on the bone is adjusted in real time when the bone is moved.

Statement 11: A surgical system is disclosed according to any of preceding Statements 1-10, further comprising a jig coupled with the bone, the jig being operable to guide a surgical blade during the cutting of the bone during surgery.

Statement 12: A surgical system is disclosed according to Statement 11, wherein the jig includes a plurality of alignment markers, wherein the controller is further operable to control the projector to project the light including one or more alignment lines to correspond with the alignment markers such that the alignment lines indicate a predetermined position of the jig based on preoperative planning.

Statement 13: A surgical system is disclosed according to any of preceding Statements 1-12, wherein the cutting line forms one or more shapes including one or more of the following: one or more dots, one or more lines, one or more circles, one or more triangles, and/or one or more irregular shapes.

Statement 14: A method is disclosed comprising: receiving, from a camera, images and/or video; tracking, by a controller, movement of bone in real-time during surgery based on the images and/or video captured by the camera; and projecting, by a projector, light including a cutting line on the bone to indicate a cutting plane for cutting the bone during surgery.

Statement 15: A method is disclosed according to Statement 14: wherein the tracking of the movement of the bone further comprises: tracking, by the controller, the movement of a tracking component of a marker coupled with the bone in the images and/or video captured by the camera.

Statement 16: A method is disclosed according to Statements 14 or 15, further comprising: registering, with the controller, a registration component of a marker coupled with the bone such that the location and/or orientation of the marker in relation to the bone is determined.

Statement 17: A method is disclosed according to Statement 16, further comprising: registering, into the controller, the location and/or orientation of the marker in relation to the bone by scanning at least a portion of a three-dimensional body of the registration component and at least a portion of the bone.

Statement 18: A method is disclosed according to any of preceding Statements 14-17, further comprising: adjusting the light projected on the bone in real time when the bone is moved.

Statement 19: A method is disclosed according to any of preceding Statements 14-18, further comprising: coupling a jig with the bone, the jig operable to guide a surgical blade during the cutting of the bone during surgery.

Statement 20: A method is disclosed according to Statement 19, wherein the light projected by the projector includes one or more alignment lines to correspond with alignment markers on the jig such that the alignment lines indicate a predetermined position of the jig based on preoperative planning.

The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the embodiments described above may be modified within the scope of the appended claims.

What is claimed is:

1. A method comprising:
   receiving, from a camera, images and/or video;
   tracking, by a controller, movement of bone in real-time during surgery based on the images and/or video captured by the camera; and
   projecting, by a projector, light including a cutting line on the bone to indicate a cutting plane for cutting of the bone during the surgery;
   wherein the light projected by the projector includes one or more alignment lines to correspond with alignment markers on a jig coupled with the bone such that the alignment lines indicate a predetermined position of the jig based on preoperative planning.

2. The method of claim 1, wherein the tracking of the movement of the bone further comprises:
   tracking, by the controller, movement of a tracking component of a marker coupled with the bone in the images and/or video captured by the camera.

3. The method of claim 1, further comprising:
   registering, with the controller, a registration component of a marker coupled with the bone such that location and/or orientation of the marker in relation to the bone is determined.

4. The method of claim 3, further comprising:
   registering, into the controller, the location and/or orientation of the marker in relation to the bone by scanning at least a portion of a three-dimensional body of the registration component and at least a portion of the bone.

5. The method of claim 1, further comprising:
   adjusting the light projected on the bone in real time when the bone is moved.

6. The method of claim 1, further comprising:
   coupling the jig with the bone, the jig operable to guide a surgical blade during cutting of the bone during surgery.

7. A method comprising:
   receiving, from a camera, images and/or video;
   coupling a jig with a bone, the jig operable to guide a surgical blade during the cutting of the bone during surgery;
   tracking, by a controller, movement of the bone in real-time during surgery based on the images and/or video captured by the camera; and
   projecting, by a projector, light including one or more alignment lines to correspond with alignment markers on the jig such that the alignment lines indicate a predetermined position of the jig based on preoperative planning.

8. The method of claim 7, wherein the tracking of the movement of the bone further comprises:
   tracking, by the controller, movement of a tracking component of a marker coupled with the bone in the images and/or video captured by the camera.

9. The method of claim 7, further comprising:
   registering, with the controller, a registration component of a marker coupled with the bone such that location and/or orientation of the marker in relation to the bone is determined.

10. The method of claim 9, further comprising:
    registering, into the controller, the location and/or orientation of the marker in relation to the bone by scanning at least a portion of a three-dimensional body of the registration component and at least a portion of the bone.

11. The method of claim 7, wherein the light projected by the projector includes a cutting line on the bone to indicate a cutting plane for cutting the bone during surgery.

* * * * *